(12) United States Patent
Golding, Jr. et al.

(10) Patent No.: US 9,771,703 B1
(45) Date of Patent: Sep. 26, 2017

(54) INTEGRATED WATERPROOFING AND DRAINAGE SYSTEM WITH INTRINSIC LEAK DETECTION

(71) Applicants: Aaron Golding, Jr., Derby, NY (US); George Baggs, Hamburg, NY (US)

(72) Inventors: Aaron Golding, Jr., Derby, NY (US); George Baggs, Hamburg, NY (US)

(73) Assignee: BuildTech Solutions LLC, Hamburg, NY (US)

( * ) Notice: Subject to any disclaimer, the term of this patent is extended or adjusted under 35 U.S.C. 154(b) by 0 days.

(21) Appl. No.: 14/958,124

(22) Filed: Dec. 3, 2015

Related U.S. Application Data

(60) Provisional application No. 62/148,312, filed on Apr. 16, 2015.

(51) Int. Cl.
| | | |
|---|---|---|
| *E02D 19/00* | (2006.01) | |
| *E02D 31/02* | (2006.01) | |
| *B32B 5/02* | (2006.01) | |
| *B32B 7/12* | (2006.01) | |
| *E04B 1/66* | (2006.01) | |
| *E04C 2/28* | (2006.01) | |
| *E04C 2/52* | (2006.01) | |
| *G01N 27/22* | (2006.01) | |
| *G01M 3/40* | (2006.01) | |

(52) U.S. Cl.
CPC .............. *E02D 31/025* (2013.01); *B32B 5/02* (2013.01); *B32B 7/12* (2013.01); *E04B 1/66* (2013.01); *E04C 2/28* (2013.01); *E04C 2/526* (2013.01); *G01M 3/40* (2013.01); *G01N 27/221* (2013.01); *B32B 2307/73* (2013.01); *B32B 2395/00* (2013.01); *B32B 2607/00* (2013.01); *E02D 2600/10* (2013.01)

(58) Field of Classification Search
CPC ... G01M 3/40; G01N 27/221; E02D 2600/10; E02D 31/025; B32B 7/12; B32B 5/02; B32B 2607/00; B32B 2307/73; B32B 2395/00
USPC ............................ 52/169.5, 169.14; 324/694
See application file for complete search history.

(56) References Cited

U.S. PATENT DOCUMENTS

| | | |
|---|---|---|
| 3,186,896 A | 6/1965 | Clem |
| 3,445,322 A | 5/1969 | Saiia et al. |
| 3,654,765 A | 4/1972 | Healy et al. |
| 3,888,087 A | 6/1975 | Bergland |
| 4,404,516 A | 9/1983 | Johnson |
| 4,467,015 A | 8/1984 | Clem |

(Continued)

OTHER PUBLICATIONS

Polyguard's 650 Membrane Product Data Sheet for sheet waterproofing membrane; published prior to Apr. 15, 2015; 5 pages.

(Continued)

*Primary Examiner* — Adriana Figueroa
(74) *Attorney, Agent, or Firm* — Terrence M. Wyles, Esq.; Startup IP Law, LLC

(57) ABSTRACT

A complete decreased mistake-proof high-reliability waterproofing system is revealed that integrates the waterproofing membrane, drain panel, and abrasion-protected filter fabric, using a factory-controlled process; furthermore, the system incorporates intrinsic devices for installation verification and leak-detection, and the potential for in situ mapping of the functional topography of the waterproofing installation over time.

19 Claims, 20 Drawing Sheets

(56) References Cited

U.S. PATENT DOCUMENTS

| | | | |
|---|---|---|---|
| 4,490,072 A | 12/1984 | Glasser | |
| 4,574,541 A | 3/1986 | Raidt et al. | |
| 4,704,048 A | 11/1987 | Ahlgrimm | |
| 4,720,669 A * | 1/1988 | Owen | G01M 3/16 324/557 |
| 4,725,785 A | 2/1988 | Converse et al. | |
| 4,730,953 A | 3/1988 | Tarko | |
| 4,740,757 A * | 4/1988 | Converse | G01M 3/40 324/326 |
| 4,751,467 A * | 6/1988 | Cooper | G01M 3/40 324/554 |
| 4,840,515 A | 6/1989 | Freese | |
| 4,897,313 A * | 1/1990 | Wiercinski | B32B 7/12 428/489 |
| 4,943,185 A | 7/1990 | McGuckin et al. | |
| 5,081,422 A * | 1/1992 | Shih | E04D 13/006 324/693 |
| 5,184,083 A * | 2/1993 | Groover | G01N 27/205 324/357 |
| 5,263,792 A | 11/1993 | Davis et al. | |
| 5,288,168 A | 2/1994 | Spencer | |
| 5,463,377 A | 10/1995 | Kronberg | |
| 5,540,085 A * | 7/1996 | Sakata | G01M 3/16 324/557 |
| 5,763,036 A * | 6/1998 | Terry | B32B 11/04 428/332 |
| 5,850,144 A * | 12/1998 | Howells | E02D 31/004 324/557 |
| 6,331,778 B1 | 12/2001 | Daily et al. | |
| 7,292,155 B2 | 11/2007 | Vokey et al. | |
| 7,488,523 B1 * | 2/2009 | Muncaster | B32B 11/04 404/17 |
| 7,686,903 B2 | 3/2010 | Muncaster et al. | |
| 7,872,479 B2 * | 1/2011 | Lorenz | G01M 3/16 324/525 |
| 8,039,081 B2 | 10/2011 | Ianniello et al. | |
| 8,291,668 B2 * | 10/2012 | Iske | E02D 31/02 52/414 |
| 8,319,508 B2 * | 11/2012 | Vokey | C23F 13/02 324/522 |
| 8,566,051 B2 | 10/2013 | Gunness | |
| 9,157,828 B2 * | 10/2015 | Jaman | G01N 27/048 |
| 9,244,030 B2 * | 1/2016 | Vokey | G01N 27/20 |
| 2009/0044595 A1 * | 2/2009 | Vokey | E04D 13/006 73/1.17 |
| 2010/0141281 A1 * | 6/2010 | Johnsen | G01M 3/047 324/694 |
| 2012/0074967 A1 | 3/2012 | Vokey et al. | |
| 2014/0049247 A1 * | 2/2014 | Gunness | G01M 3/40 324/71.1 |
| 2014/0361796 A1 | 12/2014 | Vokey et al. | |

OTHER PUBLICATIONS

Caplinq's Technical Data Sheet for LINQSTAT XVCF-Series, published Jul. 2014; 4 pages.

National Instruments' data sheet for 6 1/2-Digit Digital Multimeter, 1.8 MS/s Isolated Digitizer, and LCR Meter, published in 2007; 5 pages.

The Concrete Society—electrical conductivity webpage; published prior to Apr. 15, 2015; 1 page.

Military Handbook: Grounding, Bonding, and Shielding for Electronic Equipments and Facilities vols. 1 and 2 of 2 volumes, basic theory, Dec. 1987; 812 pages.

Grace Waterproofing System's data sheet for Bituthene 6000 EIM, published 2014; 2 pages.

Melexis Microelectroni Integrated Systems data sheet for MLZ90129, published 2012; 60 pages.

* cited by examiner

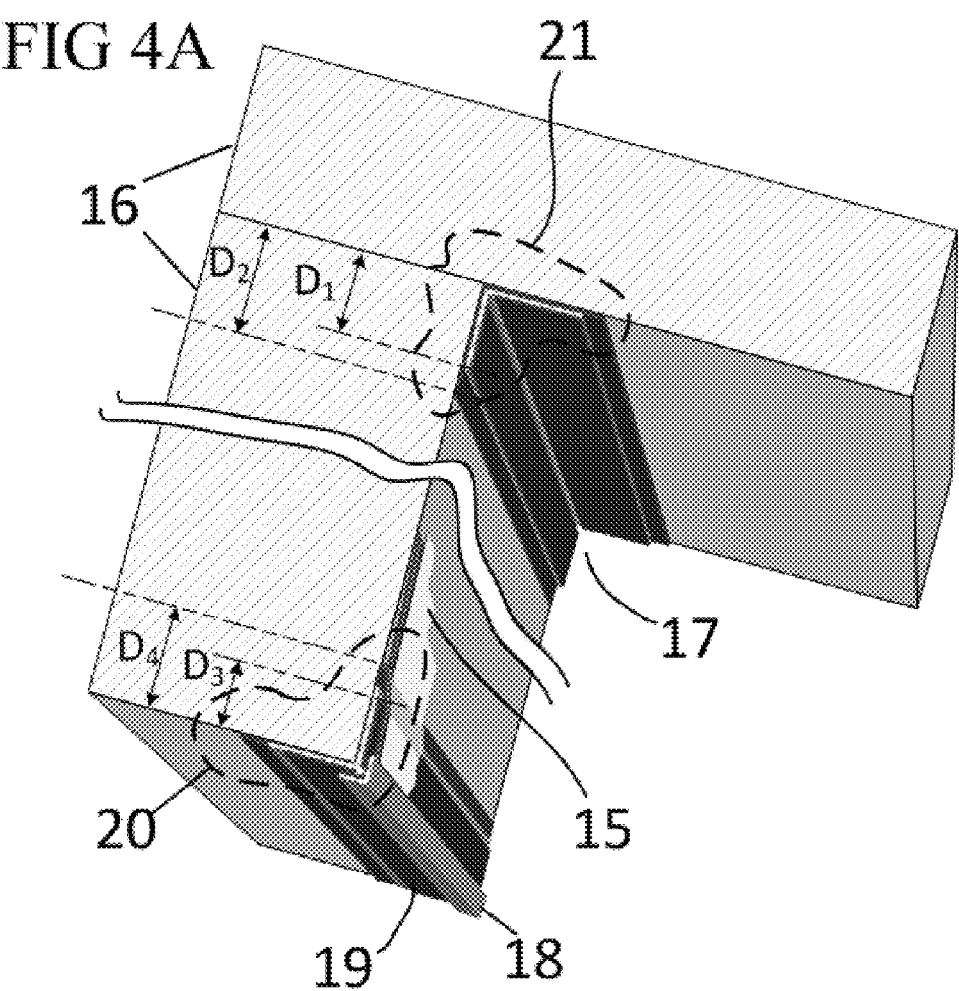

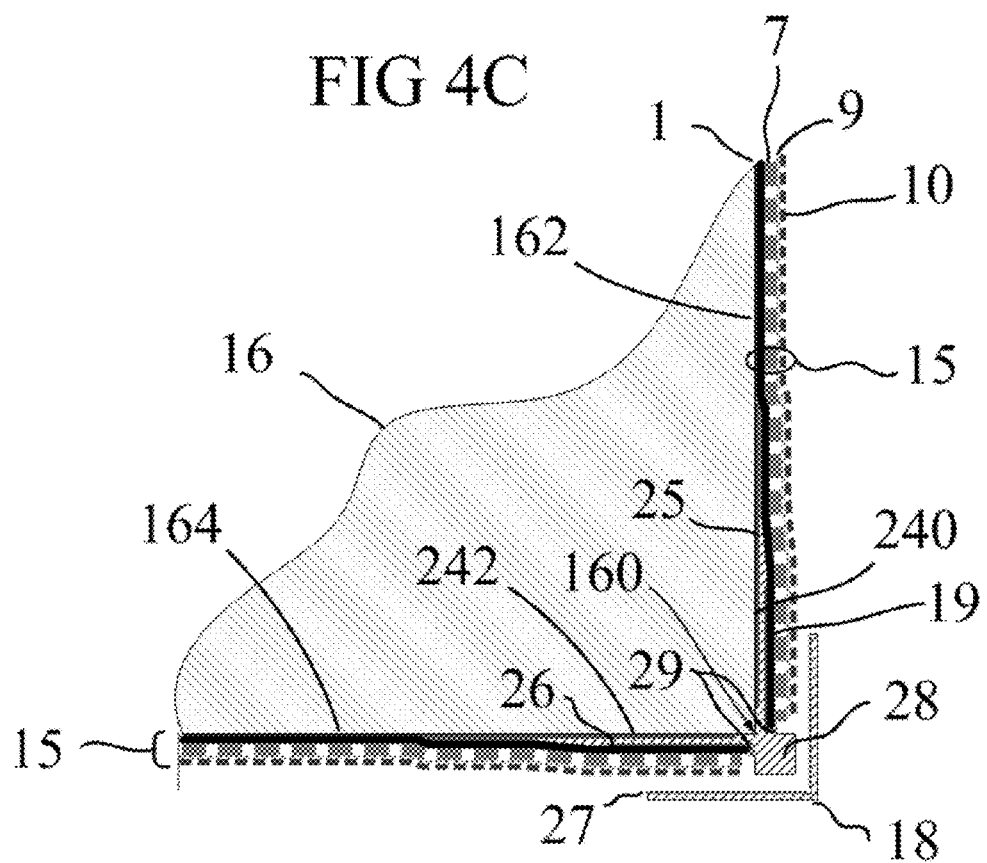

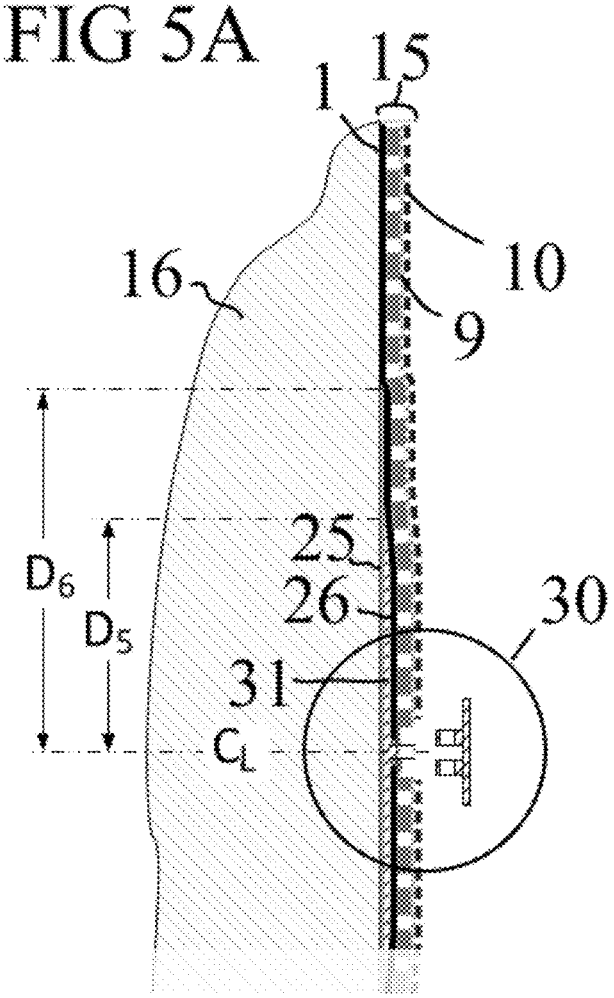

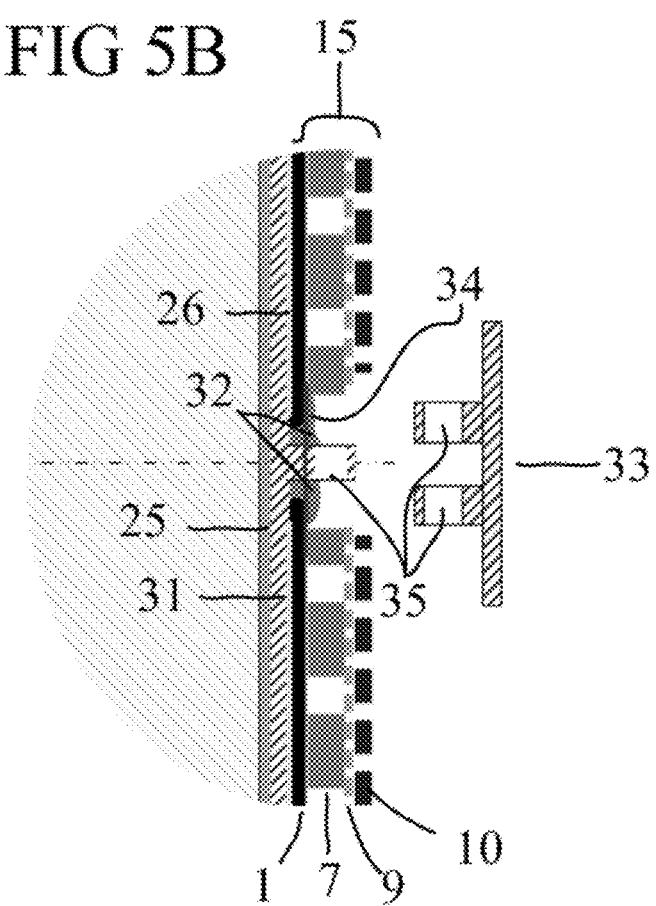

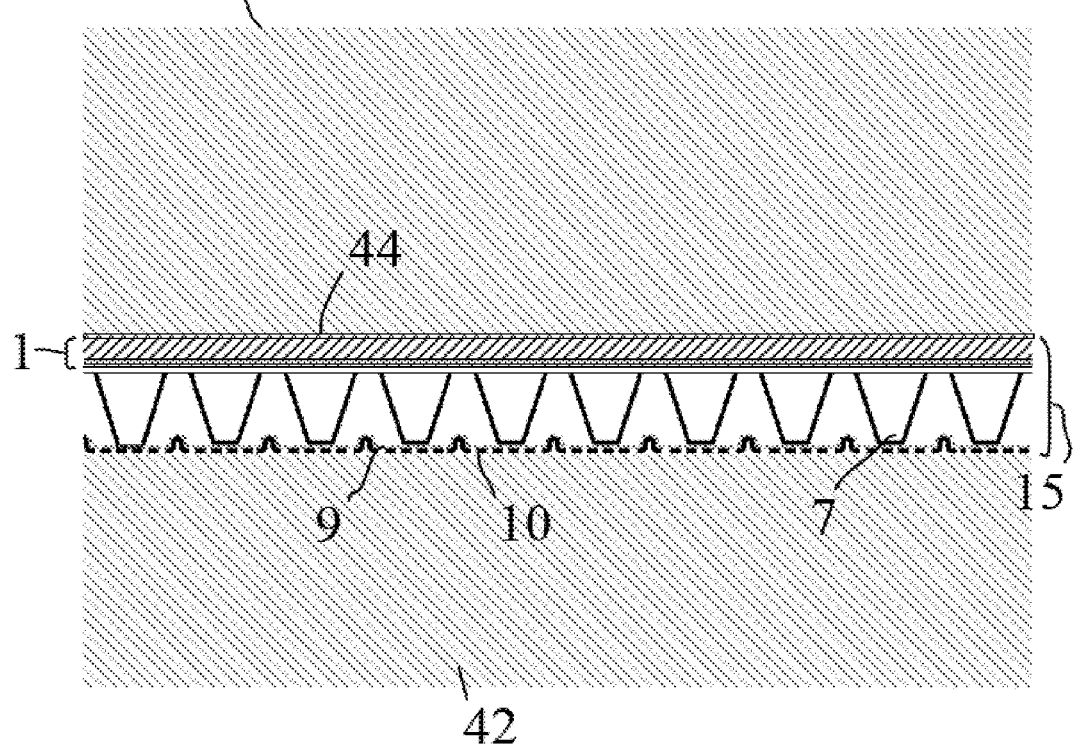

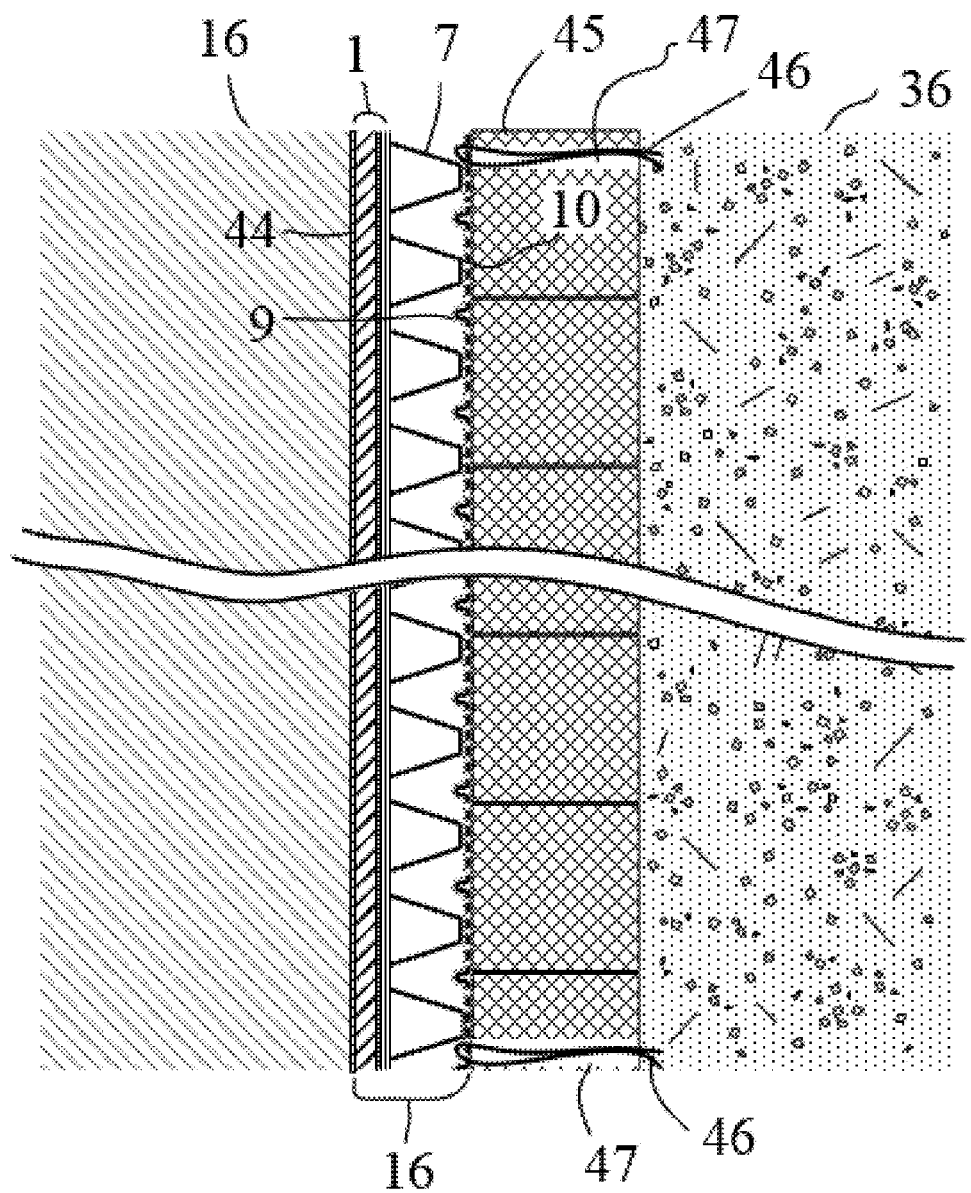

FIG 10A
FIG 10B
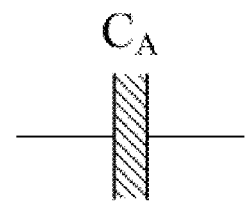
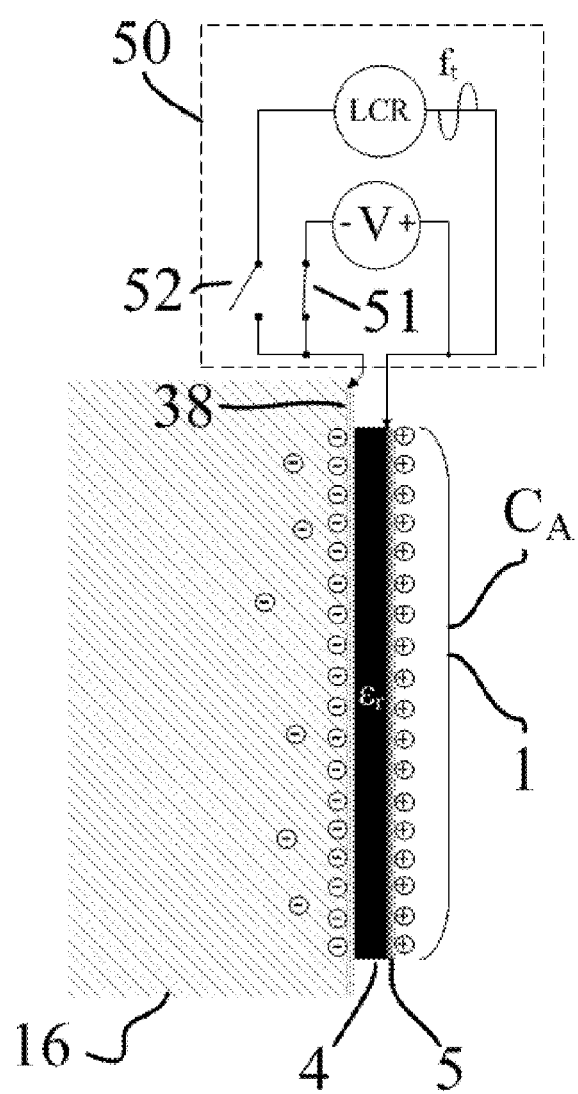

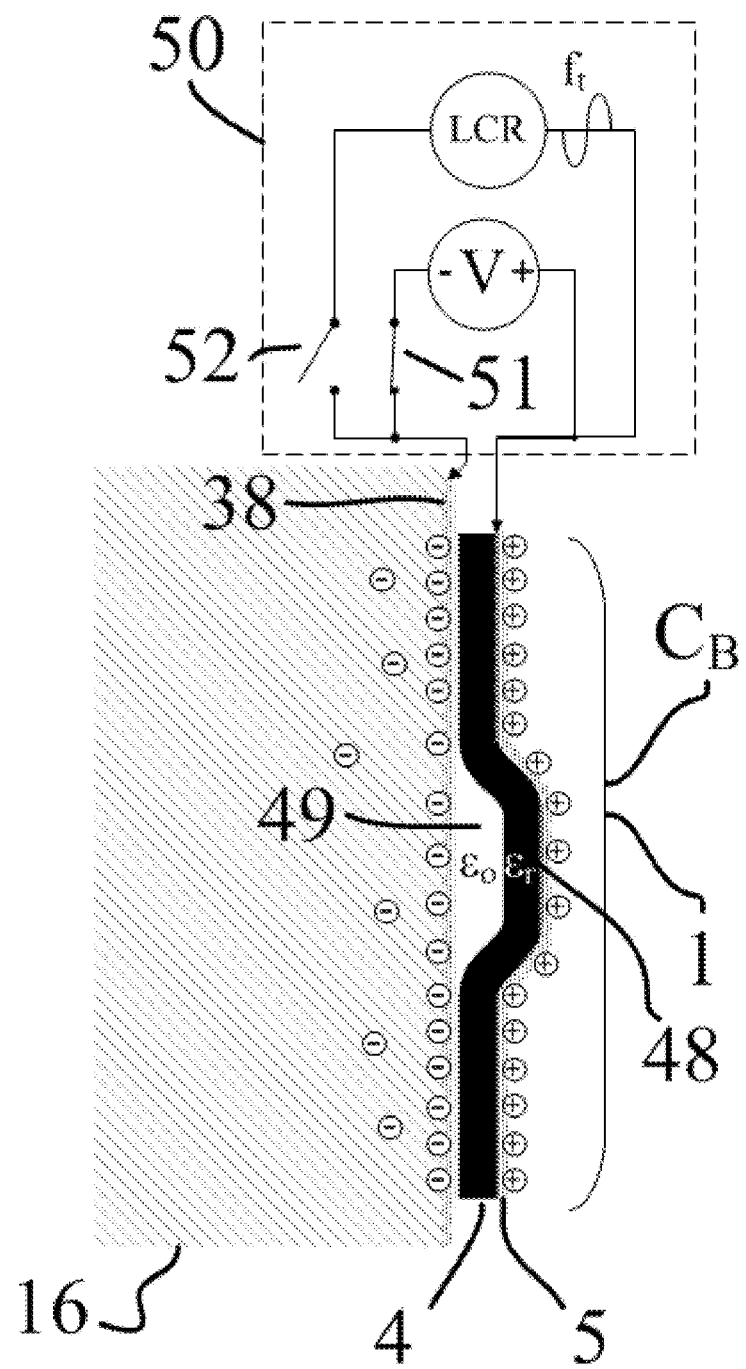

INTEGRATED WATERPROOFING AND DRAINAGE SYSTEM WITH INTRINSIC LEAK DETECTION

PRIORITY CLAIM

This application claims priority to U.S. provisional patent application Ser. No. 62/148,312, filed on Apr. 16, 2015.

FIELD OF THE INVENTION

Protecting building surfaces, especially subterranean walls and floor under slabs, from water penetration is sought.

BACKGROUND OF THE INVENTION

Prefabricated waterproofing panels or sheets using natural water absorbing materials such as bentonite clay have been disclosed in U.S. Pat. Nos. 3,186,896, 3,445,322, and 4,467,015 and used for structural waterproofing. Water activates the clay material's characteristics. The clay material is not stable over time and will eventually wash away.

Water drainage is another component of a waterproofing system. Water drainage is used sometimes in combination with the waterproofing mechanism. Separate drainage devices are disclosed in U.S. Pat. Nos. 3,888,087 and 4,490,072. To inhibit clogging of the drainage passages by soil infiltration, a filter layer is sometimes bonded to prefabricated drain panels, as disclosed in U.S. Pat. Nos. 3,654,765, 4,574,541, 4,730,953, and 4,840,515). In U.S. Pat. No. 4,704,048, Ahlgrimm discloses the use of a filter material with enough strength to resist deformation into the drainage channels by back-fill loading.

Currently, commercial waterproofing membranes are dominated by rubberized asphalt materials, while commercial drainage products are dominated by (a) a prefabricated, geocomposite panel having a polystyrene dimpled core (b) covered on one side with a polypropylene non-woven filter fabric(s). The above-identified commercial drainage products are applied over the above-identified waterproofing membrane using an applied liquid adhesive, which represents a three-step installation process—first step applies the waterproofing membrane; second step applies the adhesive; and the third step applies the drainage products, in that order.

Waterproofing membranes using this application method are susceptible to imperfections from variation in the field installation of the membrane under uncontrolled or less-than-ideal conditions; these imperfections typically appear in the form of wrinkles and voids that are termed 'fish-mouths' by those of ordinary skill in the art. These imperfections have the potential to degrade the waterproofing integrity of the installation, which will reduce functional reliability and therefore negatively impact structural warranties.

Furthermore, rubberized asphalt waterproofing membranes are sensitive to the ultra-violet (UV) spectrum of light and will chemically degrade with exposure to the sun's rays, necessitating a maximum allowed time of 30 days (see, 650 Membrane Technical Data Sheet, Ultraviolet Protection section, Polyguard® Products Inc.) before geocomposite drain panels must be installed.

Still further, despite the rugged polypropylene non-woven filter fabric material, the earthen backfill must be applied with care to prevent damage to the filter material from rocks or other discrete material that can puncture or even rip the filter fabric, thereby introducing a latent defect into the installed drainage panel. Commercial horizontal drainage panels for under slab applications use void-maintaining woven laminates and sometimes woven fabrics bonded to the crush-resistant geocomposite panels, but these are susceptible to de-bonding which would allow infiltration of poured non-hardened concrete or earth into the drainage channels.

In U.S. Pat. No. 8,039,081; Ianniello discloses a method for improving the bonding of filter material to the geocomposite panel. That disclosure, however, does not improve the protection of said filter material.

An improved drainage system structure able to resist crush and impact damage was disclosed in U.S. Pat. No. 5,263,792. In that patent, Davis taught the limitations of filter fabric with respect to keeping the drainage channels free from clogging and other impediments; however again, the filter material of this configuration would still be susceptible to damage from the application of earthen back-fill.

A combined waterproofing and drainage filter panel system was revealed in U.S. Pat. No. 4,943,185. In that patent, McGuckin disclosed that using a captured bentonite clay waterproofing material in conjunction with a structure for drainage and filtering. That system has structural and functional limitations which are stability of the waterproofing material, the mass and inflexibility of the panels, the inability to ship and store the system in rolls, and the need to secure the system to the wall that is being protected using mechanical means such as nails or tacks. Those limitations conform to the current commercial waterproofing standard configuration.

After a waterproofing system has been applied, there is no real way to verify the quality of the installation, and furthermore, functional failures can only be detected after leakage has already occurred, usually through evidence of moisture or water within the protected structure itself. Still further, location of the actual leakage point is often difficult, because water that has infiltrated a building may travel a good distance along a wall, behind the defeated water proofing membrane, before actually entering the wall (aka, structure). Even further, the problem can be compounded by water damage to the foundation of the structure and to materials or items within the below-ground levels of a building. This may explain why standard warranties on existing commercial waterproofing systems are typically only offered for one year after installation and under special conditions, only five years after installation. These issues have created the need for improved reliability of the water proofing installation as well as the necessity for leakage detection before water can damage the protected structure.

For commercial structures, electrical leak-detection methods have been developed that map the electric field potential across a conductive surface to measure the current flow to the grounded building structure along the leakage path (see, U.S. Pat. Nos. 6,331,778, and 8,566,051). To enhance leak detection, other techniques introduce a current-carrying channel external to the waterproofing barrier undergoing test, such as using an electrically conductive primer coating (see U.S. published patent application number 20140361796). While these methods are useful for above-ground horizontal waterproofing installations such as roofing, they do not address solving the below-ground leak detection problem; and while electrically-based methods for the detection of leaks have been developed to monitor for waste or chemical leakage from industrial containment facilities (see U.S. Pat. Nos. 4,404,516, 4,725,785, 5,288,168, and 6,331,778), these techniques are not suited for below-ground structural waterproofing systems.

To sense the presence of water, an electrical moisture detection mechanism using inductive coupling between a sensor and reader, or alternatively, an electrically connected sensor and reader using direct current (DC) is revealed in U.S. Pat. No. 5,463,377, while other devices (see U.S. Pat. No. 7,292,155 and U.S. published patent application number 2012/0074967) make use of tape-based or film-based sensors to detect the presence and/or location of moisture. These methods require the placement of a plurality of sensor and reader pairs in close proximity, or a plurality of electrically-connected sensors switched or linked to a single reader; furthermore, because the sensors are discrete from the monitored structure, their use requires installation either after standard waterproofing materials are applied, or to accommodate sensor placement before or during the installation of waterproofing materials, non-standard modifications to the underlying structure itself. Commercially available hand-held moisture-sensing instruments are available such as those from Tramex Ltd.; however, both the discrete sensing mechanisms and the hand-held instrumentation, cannot be used with existing commercial below-ground structural waterproofing systems.

SUMMARY OF THE INVENTION

This invention addresses the limitations of the above-identified embodiments. To eliminate the variation in installation quality from the layered multistep field-installation of commercial waterproofing systems, the job-site assembly technique is replaced with a factory-controlled process that bonds geocomposite drainage panels to waterproofing membranes prior to installation. Additionally, a filter layer of each geocomposite drainage panel is mechanically captured by a factory-applied outer perforated anti-abrasion layer made from the same material as the core of the drainage panel, which acts to protect the filter material from puncturing and tearing. Finally, the waterproofing membrane incorporates an electrically conductive layer that allows the membrane itself to serve as an electronic sensor and provide a means for installation verification through capacitance measurement, and intrinsic post-installation functional validation (i.e. leakage detection) by resistance measurement.

In a preferred embodiment, a factory-controlled process is used to bond high-impact polystyrene drainage panel cores to the polyethylene-reinforced side of a rubberized asphalt waterproofing membrane using an industrial-grade chemically-compatible organic adhesive compound, preferably a low Volatile Organic Compound (VOC) adhesive compound, and on the opposing installation side of the waterproofing membrane, there is a pressure sensitive adhesive [commonly referred to as a 'peel and stick' adhesive] release liner of silicone, or a functionally equivalent non-stick material, for easy application of waterproofing membranes to existing concrete vertical walls, and depending on the application, there are also non-pressure sensitive adhesive waterproofing membranes using a non-woven geotextile for blind-side vertical wall or underslab floor installations. The waterproofing membrane can have various thicknesses, and typically ranges between 60 to 100 mils, depending on the application. The outer side of the drainage panel opposite to the waterproofing membrane has multiple layers of non-woven synthetic filter material such as polypropylene to protect the drainage channels from soil infiltration and clogging after installation and earthen back-fill. To trap and protect the filter layer from damage, and maintain the structural integrity of the filtering and drainage system, a perforated anti-abrasion layer made from high-impact polystyrene or any functionally equivalent fungus and rot-resistant material, is attached to the dimple tops of the drainage panel core using a plurality of non-protruding polystyrene fasteners in a leak-proof configuration, as well as an industrial-grade low VOC adhesive. Because of the additional strength and mechanical stability afforded by the anti-abrasion layer, the waterproofing panel may also have pressure applied by a device such as a roller after installation. The drainage panel will also withstand normal construction traffic without damage during horizontal installations. The anti-abrasion layer also has a bend-relief feature in the form of transverse creases that provide the integrated panel with longitudinal flexibility to facilitate storage and shipment in rolls.

The pressure sensitive adhesive drainage panel with an integrated filter, offers the advantage of replacing the field-applied wet adhesive with a factory-controlled adhesive layer, thereby negating the need for application of the wet adhesive in the field, and eliminating the variations in curing times and quality of the wet adhesive that typically arise from environmental factors such as ambient temperature, humidity and particulate contamination resulting from wind-borne material such as dust and various types of organic matter. Furthermore, because the waterproofing drainage panel also includes the anti-abrasion protective layer, the added lateral stability during installation effectively eliminates the conditions favoring the creation of wrinkles and fish mouths in the waterproofing membrane.

Panel-to-panel vertical seams are sealed with overlapping end laps that create a fully adhered bond between waterproofing membranes, along with an overhanging filter and anti-abrasion layers feature that extends past the dimple top, shingling over the leading edges of adjacent panels, preventing soil infiltration after the system has been installed. Panel-to-panel horizontal seams are made using factory-made polystyrene core field joints that have a self-adhesive peel-and-stick rubberized asphalt backing and a single or double-sided adhesion flaps that form watertight interfaces to each panel's waterproofing membrane, as well as pressure sensitive adhesive strips on the upper surface of the joint that act to reinforce the membrane termination. To provide protection after the horizontal joint has been detailed, a polystyrene cap strip is installed afterward, which also serves to prevent soil infiltration into the drainage panel core. Additionally, the system provides factory-made inner and outer corner vertical end-laps with a core structure and termination method identical to the horizontal panel field joint, and these inner and corner end-laps are compliant to variations in the corner angles of the substrate. Furthermore, the inner corner end-lap may also be used horizontally as the termination joint at the wall-to-footer Interface. The field joint, end-lap and footer termination structures are designed to facilitate the application of detailing cant beads at the exposed membrane end-seams. Finally, vertical panel seams from cuts made in the field are over-lapped with composite strips of anti-abrasion material and filter fabric to seal these irregular joint openings.

A variety of factory-made standardized accessories allows for the accommodation of penetrations and other variables encountered during installation. For single penetrations, standardized half-pieces are used to fit around the penetrating pipe or conduit, and these have panel interfaces that are similar to those used for the vertical and horizontal terminations described above. For multiple or irregular penetrations, a cofferdam may be installed around the penetrations using a selection of various lengths of corner pieces, with panel-sided interface features similar to those described above. A dam feature is incorporated that acts as a form to allow liquid waterproofing material to be poured around the penetrations and to be held in place until the material has cured.

When installed on a properly detailed and primed substrate, this waterproofing system is designed to eliminate the typical quality problems arising from the human-factor and environmental variation during field installation. The factory-controlled process that integrates the waterproofing membrane and drainage panel, facilitates an inherently wrinkle and void free application of the membrane to the substrate. Furthermore, only one process step—the pressure sensitive adhesive operation—is required during the installation, thereby saving labor hours and significantly reducing the time required to finish the job. The variety of factory-made field joints allows high-quality terminations and panel unions to be made at the inside and outside corners, footers and between panels, while the integrated drain panel provides built-in UV protection of the waterproofing membrane, which helps to simplify construction logistics since the waterproofing installation need not be buried within the typical 30 to 60 days. Furthermore, the integrated anti-abrasion layer eliminates any concerns of damage to the filter fabric during the earthen back-fill operation because any damage to a conventional drainage board filter layer that happens during the back-fill operation will not be detected until water stops flowing and hydrostatic pressure increases due to sediment-clogged drainage passages. For these reasons, the term 'Poka-Yoke' (mistake-proofing a process) can be applied to this waterproofing system. In the preferred embodiment, an electrically-conductive film of conductive-particle infused polyethylene augmented with strips of metallic mesh, is integrated onto the drainage panel side of the water proofing membrane under the protective polypropylene backing film, into which a continuous DC or time-varying AC low-voltage potential is introduced via an electrical interface at the top of the waterproofing panel. This conductive layer is used to provide the means for making the electrical measurements necessary for installation verification and functional validation by leakage detection of the waterproofing system. It should be recognized that a sufficiently fine metallic mesh, foil or film may also be used to form the conductive layer itself without altering the function of this invention.

To prepare a concrete wall for the application of a waterproofing system, the already-leveled and detailed concrete substrate is coated with a primer to seal the substrate. The preferred embodiment for installation on existing vertical walls uses an electrically conductive primer, which is chemically compatible with the rubberized asphalt waterproofing membrane, and exhibits a surface resistivity after application of between 50,000 and 250,000 ohms-per-square. It must be noted that the electrically conductive primer is necessary for the installation verification measurement, but it would not be required for the leakage detection measurement; additionally, for blind-side installations and underslab applications where the non-woven geotextile is used instead of the pressure sensitive adhesive release liner, the conductive primer is not required; in these applications, the concrete wall or floor is poured in place against a pre-installed waterproofing system and for both of these applications without conductive primer, the leak detection measurement will still function.

AC voltage is used to assess the waterproofing membrane's dielectric behavior through the measurement of the capacitance between the electrically conductive layer and the electrically primed substrate, and this provides information about the mechanical integrity of a waterproofing membrane's installation against the concrete substrate. DC voltage is used for the detection of moisture leakage through the waterproofing membrane, via measurement of the electrical resistance between the conductive layer and the protected structure's earth ground. For both measurements, either temporary or permanent electrical connections are made to the conductive waterproofing membrane's conductive layer and the substrate or building earth ground.

The capacitance measurement is made using an off-the-shelf instrument such as an LCR meter, and this operation would be performed immediately after an installation, preferably before the back-fill is applied, allowing any detected problems to be quickly addressed. The measurement may also be performed after the back-fill operation as a final check that the dielectric characteristics of the waterproofing system are within specification.

The resistance measurement may be made by a variety of methods such as a hand-held ohmmeter or with longer-term in-place more customized instrumentation. Passive Radio Frequency Identification (RFID) based sensors with anti-collision capability, electrically connected to each waterproofing panel, would facilitate a fast survey of the waterproofing installation using a RFID reader. Each installed waterproofing panel would be identified by a unique code embedded on the RFID sensor device connected at or near the top of each water proofing panel, or alternatively, just below ground level in a credit card sized or smaller environmentally-protected enclosure. The waterproofing panels would be interrogated remotely using a hand-held reader device carried by an operator walking along the wall after the waterproofing system has been installed after the wall is buried by earthen backfill as a quality control verification that the initial waterproofing installation is leak-free. Additionally, the interrogation operation could be repeated by an operator at regular intervals, or continuously using automatic data-logging equipment, to allow the integrity of the waterproofing system to be validated over time. All measurements made through remote operator-based interrogation could be stored in a digital memory device in the hand-held reader for later transfer to a computerized database. The initial measurements after installation and subsequent measurements over time would create a measurement topography for each building that would be compared using regression or using other commonly applied statistically-based methods for determining trends.

Periodic measurements, made possible by the intrinsic leak detection capability of this waterproofing system and performed over the life of the building, could be part of a 'smart-building' concept facilitated by the 'Internet of things', where data is collected by a computer via either a Local Area Network (LAN) and/or over the Internet via a TCP/IP connection, and automatically monitored using Statistical Process Control (SPC) as commonly practiced in the manufacturing industry, which would allow anomalies in the data to be identified before a physical leak progresses far enough to actually breach a protected structure's foundation. SPC in conjunction with sophisticated Digital-Signal Processing (DSP) techniques would be used to identify the potential for failures, predict the life of the waterproofing installation, and perform diagnostic self-checks on the intrinsic leak-detection sensors. The level of electronic leak detection, monitoring and remote sensing used for a waterproofing system would provide the empirical data necessary

7 for rigorously establishing the scope and duration for warranty coverage against water leakage and infiltration.

DESCRIPTION OF THE DRAWINGS

The illustrations included herein are described as follows:

FIG. 1A shows an exploded view of a corner section the waterproofing panel membrane with its various components, while

FIG. 4A provides installation details of the waterproofing system with inside and outside corner assemblies, while FIGS. 4B and 4C shows cross-sectional details of the inside and outside corner assemblies.

FIG. 5A shows a cross-sectional view of a horizontal field joint that will be used to join drain panel assemblies end-to-end, while FIG. 5B shows the detail of the field joint itself.

FIG. 7A provides a view of a vertical installation of the drain panel assembly on an existing concrete wall, while

FIG. 8 provides a cross sectional view of a horizontal underslab installation of the drain panel assembly.

FIG. 9 provides a cross sectional view of a vertical blindside installation of the drain panel assembly.

FIG. 10A provides an abstract rendering of the installation verification of the waterproofing membrane using a capacitance measurement, while FIG. 10B shows the equivalent capacitor of this configuration.

FIG. 11A provides an abstract rendering of the installation verification using a capacitance measurement when there is a void between the waterproofing membrane and the concrete wall, while

DETAILED DESCRIPTION OF THE INVENTION

Figure 1A:
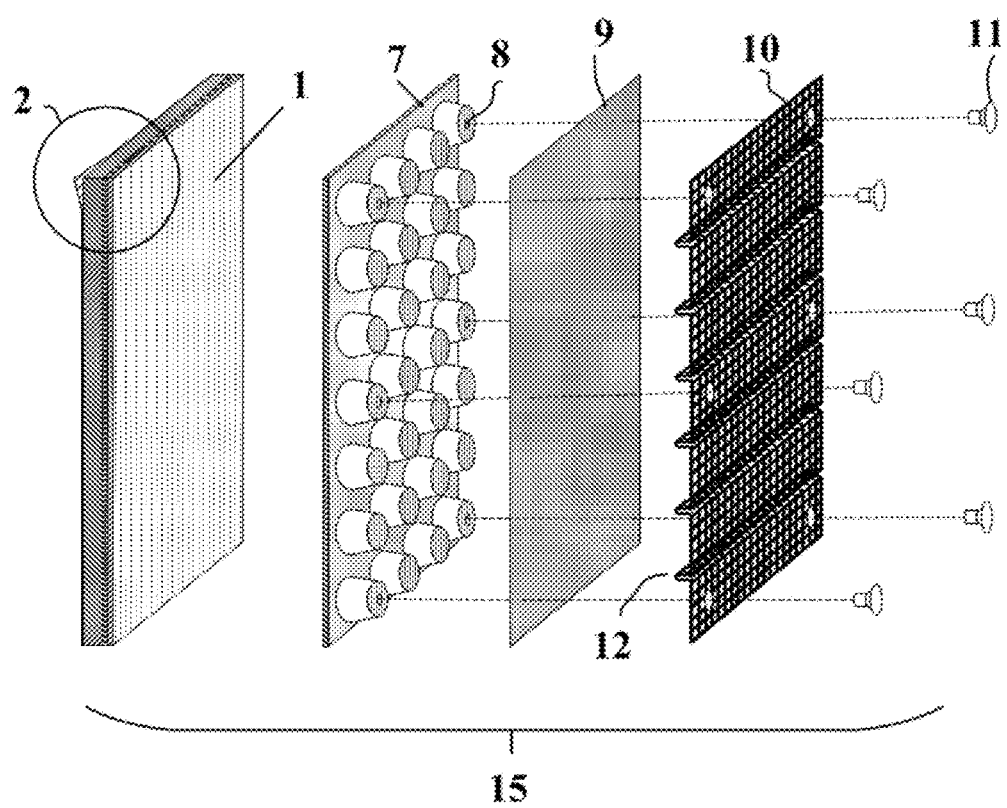
Figure 1B:
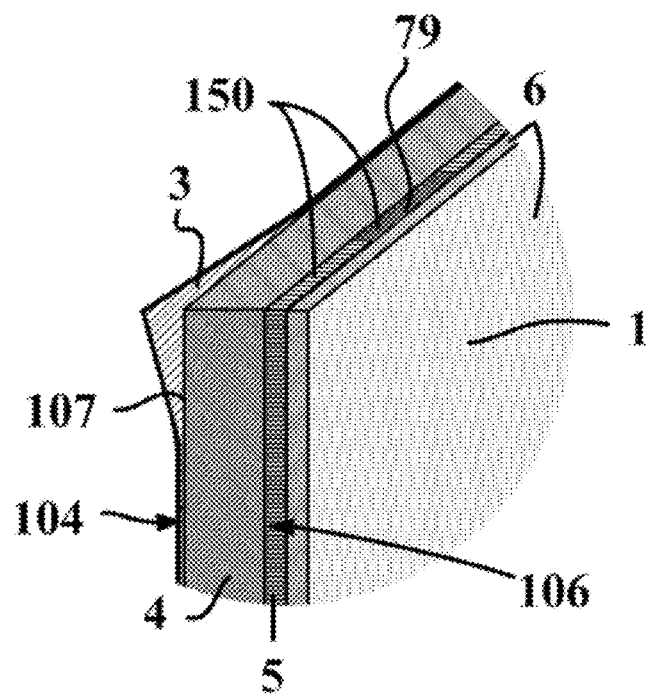
FIG. 1B shows the details of the waterproofing membrane with its various layers, and FIG. 1C which shows the structure of the conductive components inside the waterproofing membrane.
Figure 1C:
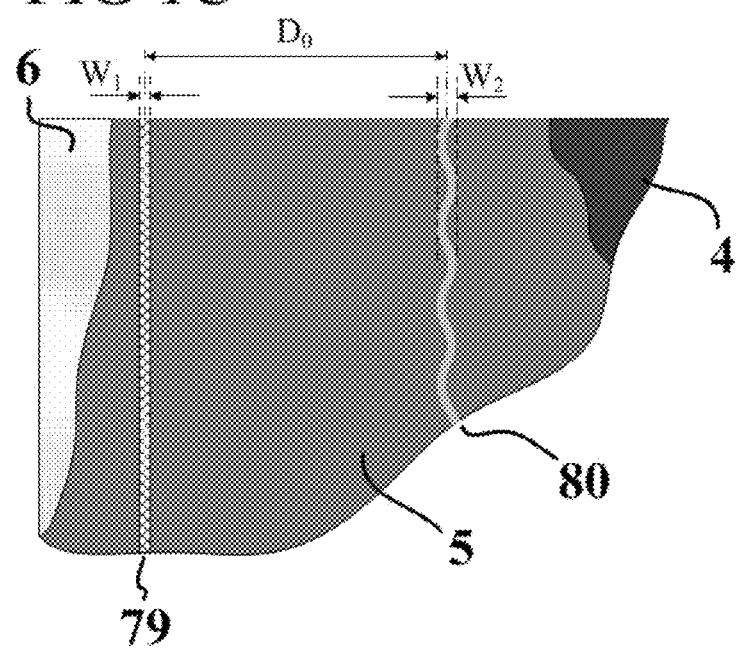

FIG. 1A shows an exploded view of a corner section of a waterproofing panel assembly 15. FIG. 1B shows an enlarged view of a composite waterproofing membrane 1 as set forth in circle 2 from FIG. 1A. FIG. 1C shows an enlarged view of conductive components inside the waterproofing membrane 1. It must be noted that these illustrations, including FIG. 2 through FIG. 9 are not to scale and are simply intended to convey the mechanical structure of the invention.

The waterproofing panel assembly 15 illustrated at FIG. 1A has the composite waterproofing membrane 1, a drain board core 7, a filter fabric 9, an anti-abrasion layer 10; and a plurality of flat-topped high-impact polystyrene rivets 11.

The drain board core 7 can have a plurality of flat-topped dimples 8. The flat topped dimples are a high-impact polystyrene with the ability to withstand a compressive loading of at least 18,000 lbf/ft$^2$ and provide a gravity-assisted water drainage flow of no less than 20 gallons/minute per foot of cross-sectional width.

The filter fabric 9 is a non-woven polypropylene material. Preferably, the filter fabric 9 is multiple layers of non-woven polypropylene material.

The anti-abrasion layer 10 is a perforated high-impact polystyrene sheet, preferably at least 60 mils in thickness. The anti-abrasion layer 10 allows a water flow rate of no less than 100 gallons/minute per ft$^2$ of area, with a plurality of transverse creases 12 to provide longitudinal flexibility.

As shown at FIG. 1B, the composite waterproofing membrane 1 has a rubberized asphalt layer 4. The rubberized asphalt layer 4 has a proximal (aka, interior) surface side 104 positioned to be closer to a building wall, and a distal (aka, exterior) surface side 106 positioned on the opposite side of the interior surface side 104 as illustrated at FIG. 1B. The rubberized asphalt layer 4 is commonly a mixture of rubber and asphalt—also called bitumen—and is reinforced on or over the exterior surface side with a high-density polyethylene (HDPE) cross-laminated film backing 6. Positioned on or under the interior surface side 104 is a pressure sensitive rubberized asphalt adhesive coating 107 protected by a release liner 3.

The terms "over" and "under" are relative terms. For example, the pressure sensitive rubberized asphalt adhesive coating is, in the claims and this specification, positioned "under" the proximal surface side because the proximal surface side is designated the composite waterproofing membrane's base. So when the proximal surface side is, for example, positioned below a basement floor or a slab, the pressure sensitive rubberized asphalt adhesive coating is actually over the proximal surface side, yet the pressure sensitive rubberized asphalt adhesive coating is still "under", for this application's purpose and the claim's interpretation, the proximal surface side since the proximal surface side is designated the composite waterproofing membrane's base. This paragraph is meant to clarify the meaning of the terms "over" and "under" as used in the application.

The release liner 3 is a non-stick material such as silicon or treated paper. Alternatively and depending on the application, the pressure sensitive rubberized asphalt adhesive coating 107 and release liner 3 may be replaced with a non-woven polypropylene fabric material.

An electrically-conductive membrane layer 5 is laminated between the rubberized asphalt layer 4 and the outer reinforcing film backing 6. Furthermore, a plurality of metallic strips 79 approximately 0.5 inches in width are laminated between the electrically conductive membrane 5 and the HDPE (high-density polyethylene) cross-laminated film backing 6. The plurality of metallic strips are longitudinally positioned in the waterproofing membrane 1, and are spaced transversely a predetermined distance. That predetermined distance is preferably every 8 inches or thereabouts. The overall thickness of the composite waterproofing membrane 1 will range between 60 and 100 mils depending on the application.

In a preferred embodiment, the electrically conductive membrane layer 5 has an additional thin layer of carbon impregnated HDPE film typically 2 to 3 mils in thickness that is chemically compatible with the rubberized asphalt, with a surface resistivity of approximately 500 ohms per square. A product called LINQSTAT XVCF made by Caplinq Corporation is ideal for this application.

The metallic strips 79 are ideally composed of Type 316 type stainless steel with a count ranging from 80 to 120 wires per inch, and wire diameter less than 5 mils, although metalized plastics such as aluminum coated polypropylene film or purely metal films such as aluminum foil may also be used to provide the same function.

Together, the electrically conductive membrane layer 5 and the woven metal mesh strips 79 form a sensing element 150 within the composite waterproofing membrane 1, where (a) the electrically conductive membrane layer 5 provides generally conductive layer throughout the waterproofing membrane, while (b) the woven metal mesh strips 79 improve the conductivity along the length of the waterproofing membrane 1 roll, and also provide an electrical connection point to the membrane 1. The dimensions and spacing of the conductive film 5 and metal mesh strips 79 may be altered without changing or altering the function of these components. Similarly, different conductive materials such as metalized plastic films and metallic foils may also be substituted for either component without substantially altering the electrical function of the sensing element.

FIG. 1C reveals how the metallic strips 79 are arranged within the composite waterproofing membrane 1 and shows a corner fragment of the composite waterproofing membrane 1. The view of this illustration is a view of the exterior side surface of the of the waterproofing layer 1 wherein most of the cross laminated HDPE backing layer 6 is shown peeled away except for the fragment to the left. The peeled away backing layer 6 exposes the electrically conductive membrane 5. A small portion of the electrically conductive membrane 5 is also peeled away to expose the rubberized asphalt waterproofing layer 4 below.

The metal mesh strip 79 with width $W_1$ of the preferred embodiment appears above the electrically conductive membrane 5, because the metal mesh strip 79 is laminated between the electrically conductive membrane 5 and the cross laminated HDPE backing layer 6 (which peeled away). An optional metalized foil or plastic strip 80 is also shown for reference purposes, and in this view, the metalized of side of the plastic strip is oriented downward to make electrical contact with the electrically conductive membrane 5. Furthermore, the foil or metalized plastic strip 80 is shown with a rounded zigzag pattern to provide longitudinal strain relief within the composite waterproofing membrane 1, and the magnitude of the pitch of this zigzag pattern would be defined by width $W_2$. The distance between the center-lines of the metallic strips is defined by distance $D_0$; in the preferred embodiment, width $W_1$ is 0.5 inches and distance $D_0$ is 8 inches. It should be understood that these dimensions may be altered to optimize the characteristics of the sensing elements within the composite waterproofing membrane 1 for maximum performance of the associated external electronic measurement devices.

Figure 2:
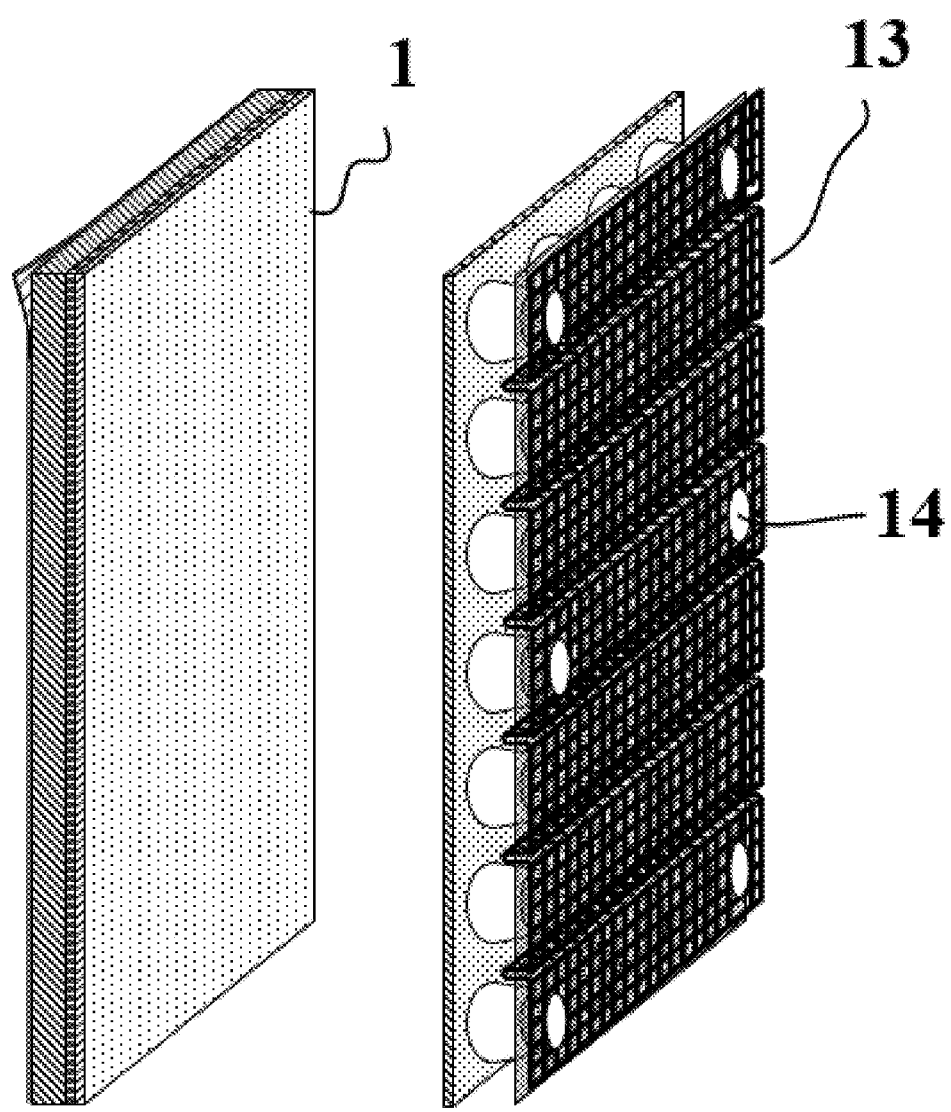
FIG. 2 provides a view of a section of the waterproofing membrane and the drain panel assembly.

Referring to FIG. 2, that Figure shows a corner section of the composite waterproofing membrane 1 and the assembled geocomposite drain panel 13 (which is the drain board core 7, the filter fabric 9, and the anti-abrasion layer 10) with installed 14 reinforcing rivets 11. The filter fabric 9 has been secured between the drain board core 7 and the anti-abrasion layer 10 by using an industrial-grade chemically-compatible low volatile organic compound (VOC) adhesive to adhere to the dimple tops 8 of drain board core 7; additionally, a plurality of rivets 11 have been installed 14 through the anti-abrasion layer 10 into existing holes on a fraction of the plurality of dimple tops 8 of drain core board 7. The installed rivet 14 configuration detail is illustrated at FIG. 7B and explained in more detail herein below. Rivet 11 has been flared under the dimple of drain board core 7 to firmly reinforce the attachment of the anti-abrasion layer 10, and the industrial-grade chemically-compatible low VOC adhesive 40 has been used to fill the inside end of the dimple tops 8 of drain board core 7 to provide a leak-proof joint. Additionally, the industrial-grade chemically-compatible low VOC adhesive 40 is used at all the dimple tops 8 of drain board core 7 contact points with anti-abrasion layer 10. The ratio of the plurality of drain board core 7 dimples 8 to the plurality of rivets 11 and 14 may range between 4:1 and 10:1 depending on the application, while the preferred embodiment shown in FIGS. 1A, 2 and 3 indicate a ratio of 4:1. The mechanical pull-strength of the drain board core 7 and anti-abrasion layer 10 preferably exceeds 400 lbf/ft$^2$.

Figure 3:
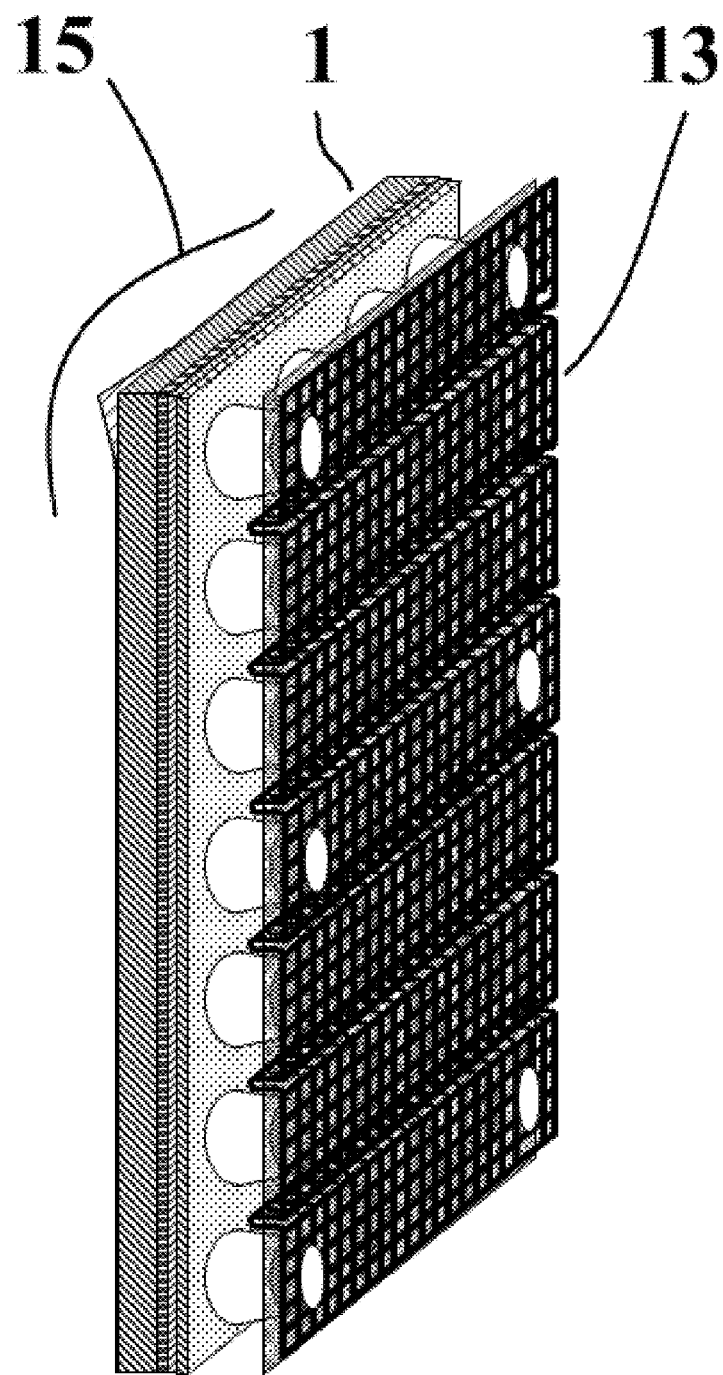
FIG. 3 shows the corner of the assembled waterproofing panel-sided.

FIG. 3 shows a corner section of the waterproofing panel assembly 15, where the geocomposite drain panel 13 has been attached to the cross-laminated film backing 6 of FIG. 1B using an industrial-grade chemically-compatible low VOC adhesive [bond strength would be typically less than 1,000 lbf/in$^2$ as applicable for non-structural adhesives]. The overall thickness of the waterproofing panel assembly 15 is approximately 0.5 to 0.6 inches [0.062+0.40+0.062, membrane+drain board core/filter+anti-abrasion layer].

Figure 4B:
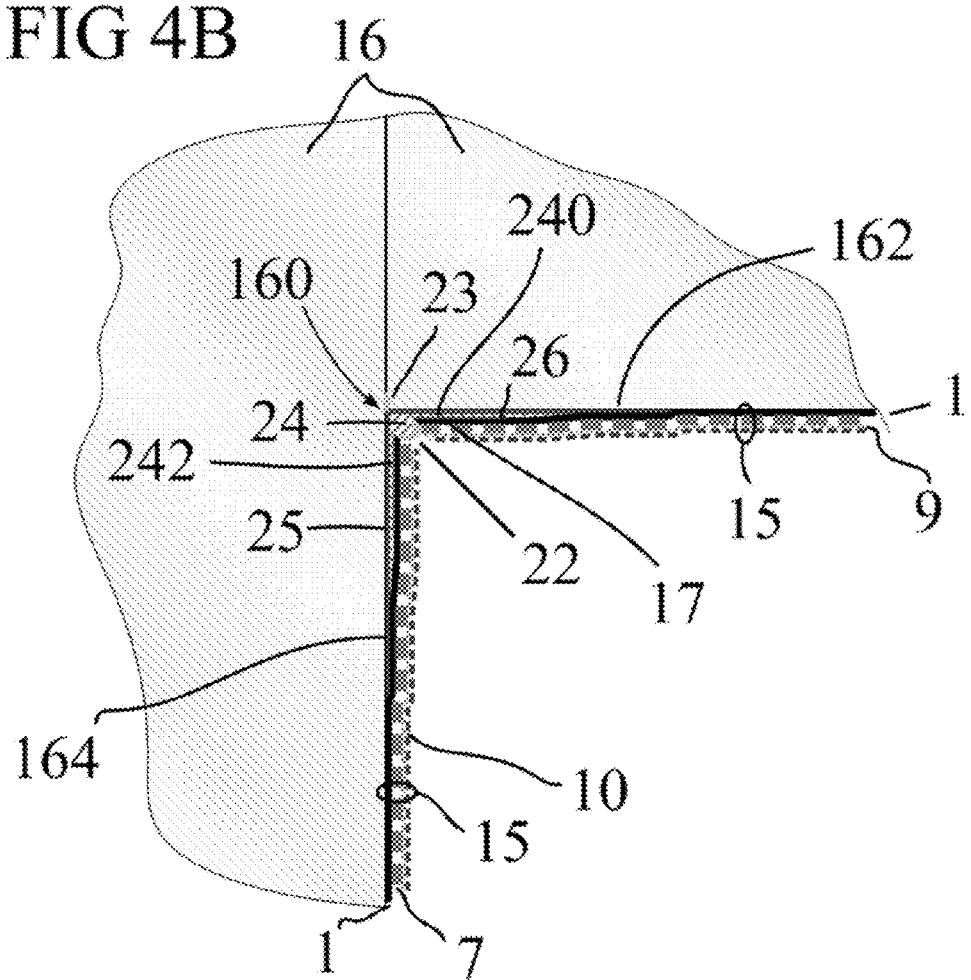

FIGS. 4A, 4B and 4C refer to installation of the waterproofing panel 15 details. FIG. 4A shows the system installed on concrete or cinder-block wall 16 while FIGS. 4B and 4C illustrate more information about outside and inside vertical corner details 21 and 20 respectively. Factory-made inside vertical corner 17 (see FIGS. 4A and 4B) and outside vertical corner 19 (see FIGS. 4A and 4C) allow waterproofing panels 15 to be joined, preferably vertically joined, at a corner 160 of the wall 16 (see FIG. 4C) or plurality of walls 16 (see FIG. 4B) to create a water-tight seal. As shown at FIGS. 4B and 4C, high-impact polystyrene cores 24 and 29 are to be positioned at the corner 160 which creates a first wall surface 162 and a second wall surface 164. The first and second wall surfaces 162, 164 can be at 90 degree angles as illustrated at FIGS. 4a and 4b; or any angle used in a polygonic structure.

Each high-impact polystyrene cores 24 and 29 has at least two polymeric, preferably polystyrene, flaps 240, 242. The flap 240 is designed to be applied to the first wall surface 162; while the flap 242 is designed to be applied to the second wall surface 164. If the first and second wall surfaces 162, 164 are at right angles, then the flaps 240, 242 are opposed at 90 degrees. The polystyrene flaps 240, 242 are compliant and the 90 degree flap angle is easily changed to accommodate variations in the wall angle.

Each flap 240, 242 is backed with a release liner that exposes a pressure sensitive rubberized asphalt adhesive 25 to attach the vertical corner pieces 17 and 19 to the wall 16. The width of the rubberized asphalt membrane 25 on the wall 16 side of inside and outside vertical corners 17 and 19 is about 6 inches, and this is indicated by dimensions $D_2$ and $D_4$ at FIG. 4A.

There are also pressure sensitive adhesive rubberized asphalt strips 26 on the front surfaces of the polystyrene flap surfaces 240, 242 opposite the wall 16 and these create a reinforced under-lap bond with the over-lapped rubberized asphalt membrane 1 of waterproofing panel 15. The width of the inside and outside vertical corner polystyrene flaps is about 4 inches as indicated by dimensions $D_1$ and $D_3$ in FIG. 4A, and this dimension represents the length of end-lap engagement between the rubberized asphalt membranes 26 of the inside 17 or outside 19 corners and the rubberized asphalt membrane 1 of waterproofing panel 15.

Industrial adhesive and sealant such as mastic is used to detail the ends and edges of the waterproofing membrane 1 by forming vertical canted beads as indicated by FIG. 4B item 22 and FIG. 4C item 28. Prior to application of the inside vertical corner 17, the seam in wall 16 is sealed using an industrial polyurethane sealant as indicated in FIG. 4B item 23. To seal the end of the drain board core, factory-made outside 18 and inside corner caps composed of anti-abrasion material are placed over the detailed 90 degree joints using a pressure sensitive adhesive with release liner.

FIG. 5A shows a panel-to-panel horizontal seam between waterproofing panels 15 and FIG. 5B provides detail of area 30 in FIG. 5A. The seam is closed using a factory-made horizontal field joint using a similar configuration to the inside 17 and outside 19 vertical corners of FIGS. 4A, 4B and 4C except the polystyrene flaps 25 are opposed at 180 degrees from each other with a length of about 6 inches as represented by dimension $D_6$ in FIG. 5A, and attached to the polystyrene core 31 which has a pressure sensitive adhesive rubberized asphalt backing 25 and a single or double-sided adhesion flaps that form watertight interfaces to each panel's waterproofing membrane, as well as pressure sensitive rubberized asphalt adhesive strips 26 on the upper surface of the joint that act to reinforce the membrane termination. This under-lap length is about 4 inches and is indicated by dimension $D_5$ in FIG. 5A. A feature shown in FIG. 5B provides an electrical conduit 34, like a wire, to electrically connect the conductive membrane layer 5 of the composite waterproofing membrane of FIG. 1B across the horizontal joint. Horizontal canted beads of adhesive sealant such as mastic seals and protect the horizontal edges of the waterproofing panel 15 waterproofing membrane 1 as shown by item 32 in FIG. 5B. To provide protection after the horizontal joint has been detailed, a polystyrene cap strip 33 is installed to prevent soil infiltration into the drainage panel core, and also provides flow channels 35 that allow a gravity-assisted water drainage flow of no less than 20 gallons/minute per linear foot across the horizontal field joint.

Figure 6A:
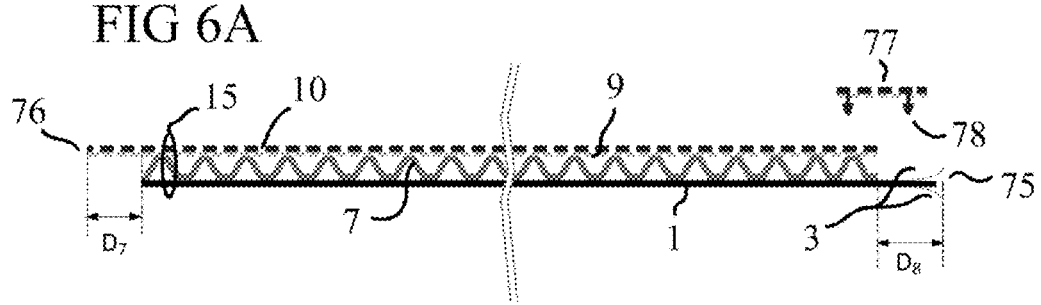
FIGS. 6A and 6B shows a cross-sectional view from above, with the upper image of FIG. 6A representing a water-proofing panel prior to installation, and the lower image of FIG. 6B representing the panel installed on a concrete wall with under and over end-lap details to adjoining panels on each side.
Figure 6B:
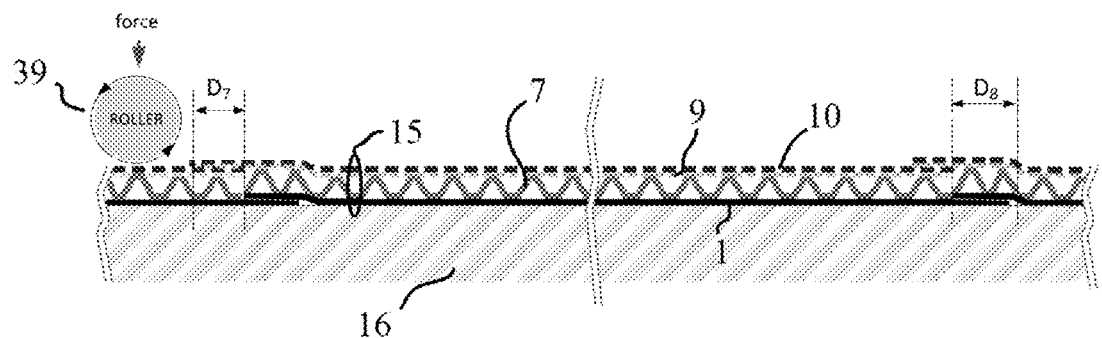

FIGS. 6A and 6B illustrates details of how the waterproofing panels 15 are vertically joined and sealed to each other. The upper image—FIG. 6A—shows a panel in the uninstalled condition, where each panel has a protruding flap 75 of composite waterproofing membrane 1 on one side extending about 4 inches as represented by distance $D_8$, with the pressure sensitive rubberized asphalt adhesive coating release liners 3 below and above the flap, and on the other side, another flap 76 extending about 3 inches as represented by distance $D_7$, of the anti-abrasion layer 10 and filter fabric layer 9 attached to drain board core 7. When the waterproofing panels 15 are installed on the wall 16 as illustrated at FIG. 6B, the composite waterproofing membrane 1 is under-lapped for distance $D_8$ below the adjacent panel's composite waterproofing membrane 1, and the anti-abrasion layer 10 and filter fabric layer 9 is over-lapped for distance $D_7$ above the opposite adjacent panel's composite waterproofing anti-abrasion layer 10. The installed waterproofing panels are rolled with roller 10 or appropriate pressure is applied to ensure adhesion on all end-lap joints. For covering irregular joints created by the necessity of cuts made in the field, a strip of anti-abrasion and filter fabric material 77 is provided with a plurality of capture features 78 to engage and lock into the waterproofing panel 15 anti-abrasion layer 10; furthermore, the capture feature 78 has a rounded end that will not damage the waterproofing panel 15 filter fabric layer 9.

Figure 7A:
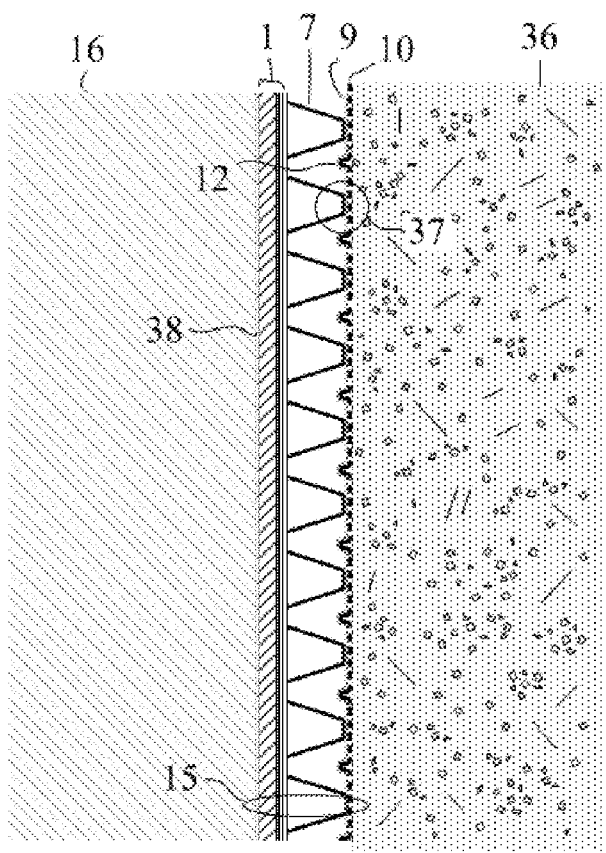
Figure 7B:
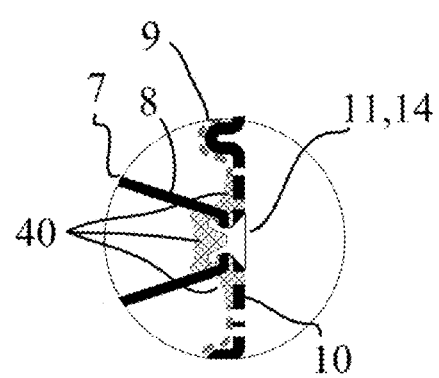
FIG. 7B shows the details of the waterproof riveting configuration between the drain panel assembly anti-abrasion layer and the dimple board.

FIG. 7A and FIG. 7B provide vertical existing wall installation details, where the concrete wall 16 and waterproofing membrane 15 are shown in cross-section view, along with earthen back-fill 36. Area 37 is shown in greater detail at FIG. 7B and was explained in the detailed description for FIG. 2 as set forth above. The waterproofing panel 15 with composite waterproofing membrane 1 is applied over a conductive primer coating 38 applied to the concrete wall 16 surface. This cross-sectional view also shows the high impact polystyrene drain board core 7 and the high impact polystyrene anti-abrasion layer 10 which protects the filter fabric layer 9 during the application of earthen back-fill 36, and also the transverse crease 12 feature in the anti-abrasion layer 10.

FIG. 8 provides details for the horizontal underslab installation, where the waterproofing panel 15 is applied prior to the pouring of concrete floor 43 with the anti-abrasion layer 10 downward. The waterproofing panel 15 with composite waterproofing membrane 1 and a non-woven polypropylene fabric layer 44 faces upwards and the floor concrete 43 is poured on top of the horizontal waterproofing panel 15. This cross-sectional view also shows the high impact polystyrene drain board core 7 and the high impact polystyrene anti-abrasion layer 10 which protects the filter fabric layer 9 during the underslab installation.

FIG. 9 provides vertical blindside installation details, where the waterproofing panel 15 is applied prior to pouring the concrete wall 16 with the anti-abrasion layer 10 facing the blindside scaffolding cross members 45. The plurality of perforations in the anti-abrasion layer 10 allow a plurality of devices 46 such as strings or tie-wraps to be used to secure the waterproofing panel 15 vertically against the scaffolding cross members 45 through a plurality of openings 46 in the scaffolding cross members 45 thereby decreasing and preferably eliminating the need to secure the panel to blindside scaffolding cross members 45 using penetrating fasteners such as nails or screws. The waterproofing panel 15 with composite waterproofing membrane 1 and a non-woven polypropylene fabric layer 44 faces towards the wall concrete 16 which is poured behind the vertical waterproofing panel 15. This cross-sectional view also shows the high impact polystyrene drain board core 7 and the high impact polystyrene anti-abrasion layer 10 which also protects the filter fabric layer 9 during the blindside installation.

FIG. 10A and FIG. 10B shows an abstraction of the installation verification using capacitance measurement on a normal waterproofing membrane and substrate configuration. The composite waterproofing membrane 1 is shown applied to a vertical concrete wall 16 onto which conductive primer 38 has been applied to the surface of the concrete wall 16. A voltage source 'V' within the test device 50 applies a DC voltage through switch 51 between the positively charged conductive membrane layer 5, and the negatively charged conductive primer 38, creating capacitor $C_A$ with dielectric permittivity $\epsilon_r$ for the rubberized asphalt layer 4. The equivalent electrical circuit for capacitor $C_A$ is shown in FIG. 10B.

$$C_A = \epsilon A/d = \epsilon_r \epsilon_0 A/d \quad (1)$$

Where:
  $\epsilon$=dielectric permittivity
  A=area of the capacitor plates
    (in this case the waterproofing membrane area)
  d=distance between the capacitor plates
    (in this case the thickness of the rubberized asphalt membrane)
  $\epsilon_r$=relative dielectric permittivity of the rubberized asphalt membrane, approximately 3
  $\epsilon_0$=dielectric permittivity of free space, 8.854 . . . E-12 Farads/meter When switch 51 is opened and switch 52 closed, the LCR meter in test device 50 measures the components of inductance (L), capacitance (C) and resistance (R) of the capacitor $C_A$ formed by the conductive membrane layer 5, the asphalt waterproofing membrane 4, and the substrate conductive primer 38 with applied AC voltage at test frequency $f_t$; furthermore, it is preferable that the LCR meter have a variable test frequency $f_t$. Additionally, because the physical configuration of the composite waterproofing membrane 1, there will be relatively large values of C and R when compared to L, and the composite waterproofing membrane 1 will behave much like a capacitor with a very high ESR (Equivalent Series Resistance). The values obtained for C and R can be used to characterize the dielectric behavior of the installed composite waterproofing membrane 1. Finally, in practical applications, only the variable frequency LCR meter is necessary to make this measurement on the composite waterproofing membrane 1; the voltage source V is only provided for illustrative purposes in FIGS. 10A and 11A to show how the composite waterproofing membrane 1 forms capacitor $C_A$ by holding electrical charge.

Figure 11B:
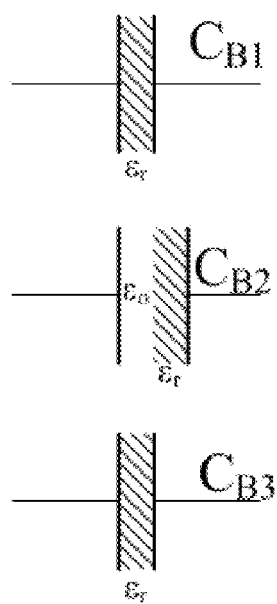
FIGS. 11B and 11C show the equivalent capacitors of this configuration.
Figure 11C:
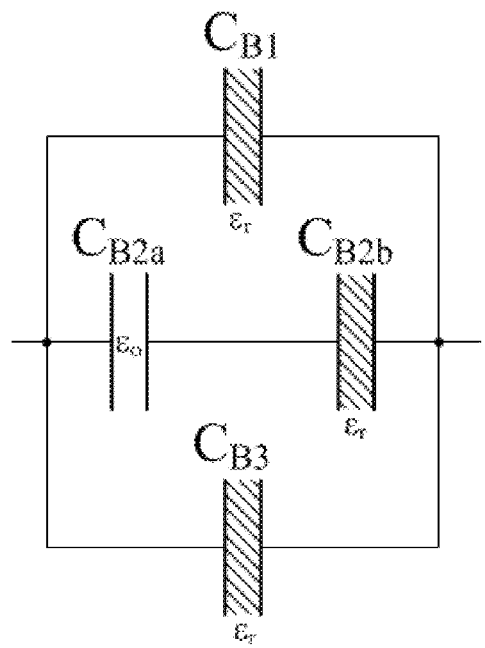

FIG. 11A and FIGS. 11B and 11C shows an abstraction of the installation verification using capacitance measurement on an abnormal defective waterproofing membrane and substrate configuration. FIG. 11A is identical to what was described for FIG. 10A except the installation of the composite waterproofing membrane 1 has been compromised by a void area 49 between the rubberized asphalt waterproofing membrane 4 and the wall 16 substrate conductive primer 38, creating capacitor $C_B$ with dielectric permittivity $\epsilon_r$ for the rubberized asphalt layer 4 and dielectric permittivity near that of free space $\epsilon_0$ for the voided area. The equivalent capacitors for the upper area without a void $C_{B1}$, and the lower area without a void $C_{B3}$, and the center area with the void $C_{B2}$ are shown in FIG. 11B. The equivalent electrical circuit for capacitors $C_{B1}$, $C_{B2}$ and $C_{B3}$ is shown in FIG. 11C.

$$C_B = C_{B1} + C_{B2} + C_{B3} \quad (2)$$

Where:
  $C_{B2}$ will always be less than the capacitance of the voided area since:

$$1/C_{B2} = 1/C_{B2a} + 1/C_{B2a} \text{ or}$$

$$C_{B2} = C_{B2a} C_{B2b}/(C_{B2a} + C_{B2b}) \quad (3)$$

And:
  $C_{B2a}$=the capacitor formed by the void 49 with dielectric permittivity $\epsilon_0$
  $C_{B2b}$=the capacitor formed by the rubberized asphalt waterproofing membrane 4 with relative dielectric permittivity $\epsilon_r$ Since the relative dielectric permittivity of rubberized asphalt has a value close to 3, and assuming the distance of the void 49 is the same as the thickness of the rubberized asphalt waterproofing membrane 4, and that the void is filled with air, using Equation (3) above, the capacitance of $C_{B2}$ with the void 49 would be 25% of the capacitance of $C_{B2}$ without the void 49. Factors such the distance and area of void 49 will effect this approximation, but the implication is that a void 49 of sufficient area would be detectable by measurements using an LCR meter as described above; furthermore, a custom-designed capacitance sensing device would provide detection capability that could be optimized to the characteristics of the composite waterproofing membrane 1.

Figure 11D:
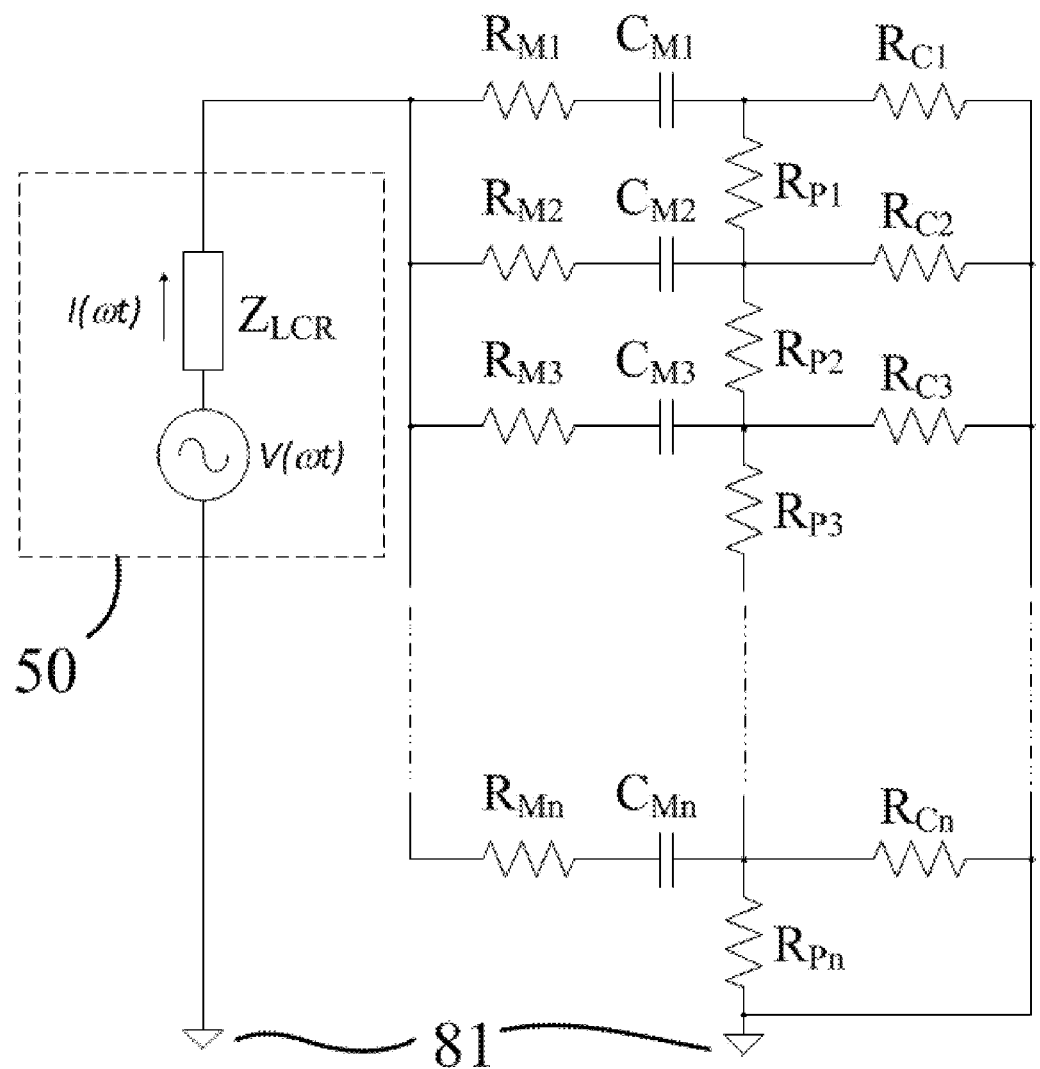
FIG. 11D shows the schematic of the electrical model for the equivalent circuit of FIG. 11A.

The schematic in FIG. 11D illustrates an approach used to computer model the method for measuring the electrical effects described in FIG. 11C. The composite waterproofing membrane 1 of FIG. 11A is represented by an n-element series of lumped element resistors $R_{Mn}$ and capacitors $C_{mn}$, where $R_M$ represents the surface resistivity of the electrically conductive layer 5 and $C_M$ represent the capacitance of the composite waterproofing membrane 1 and 'n' represents the nth element in the n-element series. $R_P$ and $R_C$ represent the surface resistivity of the electrically conductive primer 38 and volume conductivity of the concrete wall 16, respectively. The LCR device 50 provides a variable frequency AC voltage source with the capability to measure the time-varying current $I(\omega t)$ through test impedance $Z_{LCR}$, which introduces the test current into the common input node feeding the electrically conductive layer 5 elements $R_{M1}$, $R_{M2}$, $R_{M3}$ . . . $R_{mn}$ when LCR device 50 places a test voltage $V(\omega t)$ between the common input node and the electrical ground 81. It should also be noted that the common input node electrically represents the conductive metallic strip 79 shown in FIG. 1C.

The lumped element model was partitioned based on setting the distance $D_o$ in FIG. 1C to 8 inches, and using Equation (1) with a relative dielectric permittivity of 3 for the rubberized asphalt layer 4 of thickness 40 mils, implying a capacitance of 4.25 E-8 Farads or 42.5 nF of capacitance for each $C_M$ element, which normalizes to 664 pF/in$^2$; additionally, the electrically conductive layer 5 has a surface resistivity of 500 ohms per square, and the square is 8 inches by 8 inches and is electrically connected along one edge by the conductive metallic strip 79; therefore, each $R_M$ element was set to 500 ohms. Furthermore, the electrically conductive primer 38 layer has a surface resistivity of 50,000 ohms per square, so each $R_P$ element was set to 50 Kohms, assuming that each 8 inch square is continuously connected at the edges. Finally, element $R_C$ was set to 1000 ohms based a volume resistivity for the concrete equal to 1000 ohms and assuming continuous planar contact between the electrically conductive primer 38 layer and the concrete substrate 16.

The frequency response sensitivities of the gain and phase of the LCR device 50 test voltage $V(\omega t)$ and test current $I(\omega t)$ were investigated using this lumped-element high ESR capacitance model by changing a series of capacitive elements as described in Equation (3) to produce changes in lumped capacitance values within the model yielding the results summarized in Table 1 below:

TABLE 1

| Change in capacitance | D Gain (dB) | D Gain (1-Ao/Ai) | D Phase (degrees) | Effective magnitude of voided area 49 on 4' × 10' waterproofing panel |
|---|---|---|---|---|
| 5% | −0.244 | −2.8% | 1.2 | 2 square feet or an area equivalent to 17" × 17" |
| 10% | −0.5 | −5.6% | 2.3 | 4 square feet or an area equivalent to 24" × 24" |

A change in gain of nearly 6% with a phase angle difference of 2.3 degrees is certainly detectable with standard LCR instrumentation, and the nearly 3% gain and 1.2 degree phase angle change would be detectable with an LCR instrument that provides a variation in test frequency [see datasheet for NI 4072 6½-Digit Digital Multimeter, 1.8 MS/s Isolated Digitizer, and LCR Meter]. Difficulties would arise from panel-to-panel installation variation that would potentially reduce the signal-to-noise ratio of the measurement, which would determine the minimum size of a voided area that could be quantitatively detected reliably; however, statistical methods such as (but not limited) to Analysis of Variation (ANOVA) would allow a statistically out-of-family (OOF) normalized LCR measurement to be detected using the null hypothesis.

The installation verification using capacitance measurement is intended to detect areas of the composite waterproofing membrane 1 are not well attached to the concrete wall 16, but not small defects such as 'fish mouths', which is sufficient because the factory integrated nature of the waterproofing panel eliminates the possibility of defects introduced through field installation such as 'fish mouths'.

Figure 12:
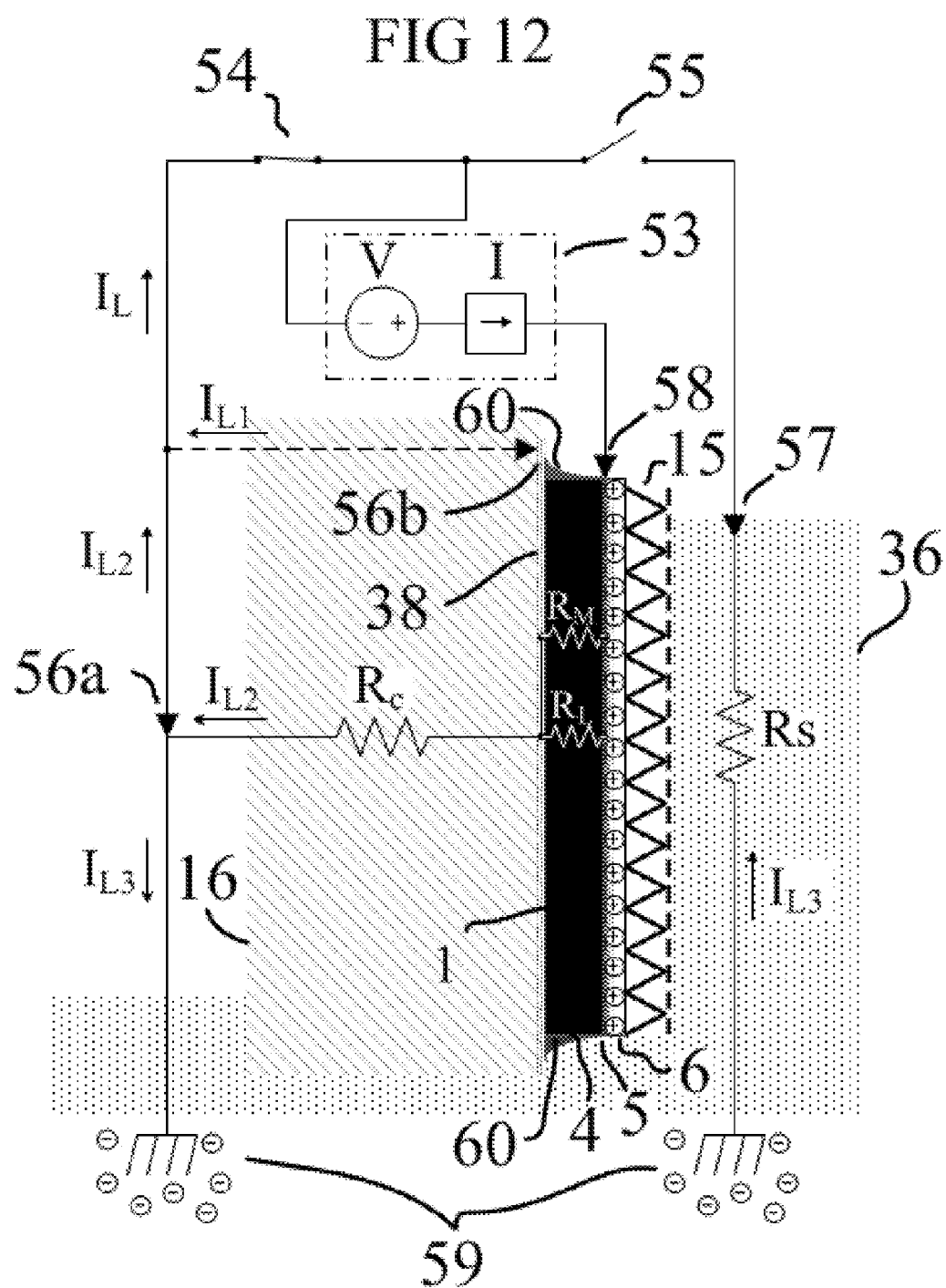
FIG. 12 provides an abstract rendering of the installation verification of the waterproofing membrane using a leak detection measurement using resistance.

FIG. 12 provides an abstraction of a leakage detection verification method using electrical resistance measurement on an installed waterproofing membrane. The waterproofing panel 15 is shown applied to a vertical concrete wall 16 onto which conductive primer 38 has been applied to the surface of the concrete wall 16. A voltage source 'V' within the sensor device 53 applies a DC voltage through switch 54 between the conductive membrane layer 5 positive connection 58, and the negative connection 56a attached to the electrical earth ground 59 of the building structure. In the preferred embodiment, a current detector I within the sensor device 53 measures the electrical leakage current $I_{L2}$ flowing in series through the resistance $R_M$ of the asphalt waterproofing membrane 5 and then through the resistance $R_C$ of the concrete structure 16. When a water leak compromises the composite waterproofing membrane 1, there will be a much lower water leakage resistance $R_L$ that will appear in parallel with the membrane resistance Rm. The measured leakage current $I_L$ will increase and provide indication that the composite waterproofing membrane 1 is either degrading or has failed. An alternate measurement path would be possible by attaching the negative connection directly to point 56b, which is the conducting primer 38 that is coating concrete wall 16 and measuring electrical leakage current $I_{L2}$; additionally, by opening switch 54 and closing switch 55, electrical leakage current $I_{L3}$ could be measured, which is the return path through structure ground 59 and earth 36 at connection point 57 instead of directly from the structure's earth ground at 56a. In both cases, the structural concrete 16 provides the conduction path between the waterproofing membrane and the structural earth ground 59. For reference, oven-dried concrete has a very high volume resistivity, but once concrete has been exposed to earth and moisture, the volume resistivity of concrete drops to between 100 and 1000 ohm-meters [information obtained from US Concrete Association]; soil volume resistivity varies with location, type and moisture levels, but typically ranges between 100 and 5000 ohm-meters [MIL-HDBK419A: GROUNDING, BONDING, AND SHIELDING FOR ELECTRONIC EQUIPMENT AND FACILITIES]; in both cases, due to the large contact areas of structures, the net parasitic resistances seen by the detection system are several orders of magnitude below the resistance of rubberized asphalt membrane material, which is typically between 100 to 200 Mohms (1.+E8 to 2.+E8 ohms) [W.R. GRACE BITUTHENE® 6000 EIM SPEC SHEET].

FIG. 12 also shows a detailing sealant material 60 covering the ends of the composite waterproofing membrane 1 which could be mastic adhesive sealant or another suitable construction sealant, and this is necessary to prevent moisture from working its way under the edges of the rubberized asphalt membrane 4 and degrading the bond with the concrete wall 16; additionally, the detailing material acts as an electrical insulator and prevents stray leakage current paths. Typically, the above-ground end of the waterproofing membrane 5 is covered by a plastic or metal termination bar, which provides mechanical protection for the edge, and also serves as a cofferdam to hold the sealant material 60 when it is first applied. In the case of the electronic leak detection configuration, the termination bar would also provide the electrical connections to the ends of the metallic strips 79 in the electrically-conductive membrane layer 5 of the composite waterproofing membrane 1 for the positive connection point of the sensor device 53 and/or the positive connection lead of the LCR instrument of device 50 in FIGS. 10A and 11A, as well as hold an electrically conductive strip against the conductive primer 38 coating the concrete wall 16, which is where the negative connection of the LCR instrument in device 50 will be made, or serve as an alternate negative connection 56b for the current leakage device 53. Because of lightning strikes to buildings which causes large amounts of electrical charge to travel to earth ground 59 through the structure's grounding system connections, high voltage surges can be present on the connection point to earth ground 56a, and therefore, the current leakage device 53 would require protection from EFT (Electrical Fast Transient) that would arise due to the inductance of the structural grounding conductors.

Figure 13:
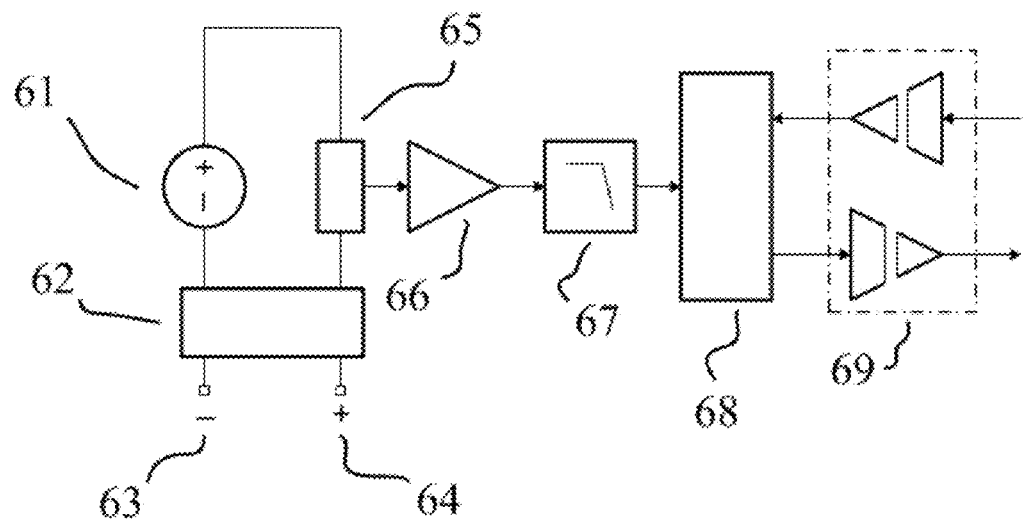
FIG. 13 shows a block diagram of the electronic leak detection method.

FIG. 13 shows the block diagram for a generic electronic device that will perform the function of the leakage detector 53 shown in FIG. 12. Voltage source 61 applies a DC potential across the composite waterproofing membrane 1 of FIG. 1B at the negative 63 and positive 64 connection points through protection circuit 62, which blocks excess external voltage that may be induced into the composite waterproofing membrane 1 from damaging the electronic detection components. Current sensing circuit 65 measures the current level leaking through the rubberized asphalt membrane 4 of FIG. 1B, and signal conditioner 66 amplifies and scales the output from the current sensing circuit 65 and passes the signal through a filtering circuit to remove electronic noise before the signal is read by the data processing module 68. A transceiver device 69 allows the processing module 68 to transmit leakage data to a remote receiver and also receive commands from a remote transmitter. The device represented by FIG. 13 may take several different forms including but not limited to: a handheld off-the-self ohmmeter where the operator performs the functions of the remote reader and command unit; a current leakage detector that transmits data over a dedicated or networked hardwired interface; a remotely linked data logger; a stand-alone battery-powered recorder; a wireless device that transmits and receives information through a radio frequency link; and/or a computerized data acquisition and control system.

Figure 14A:
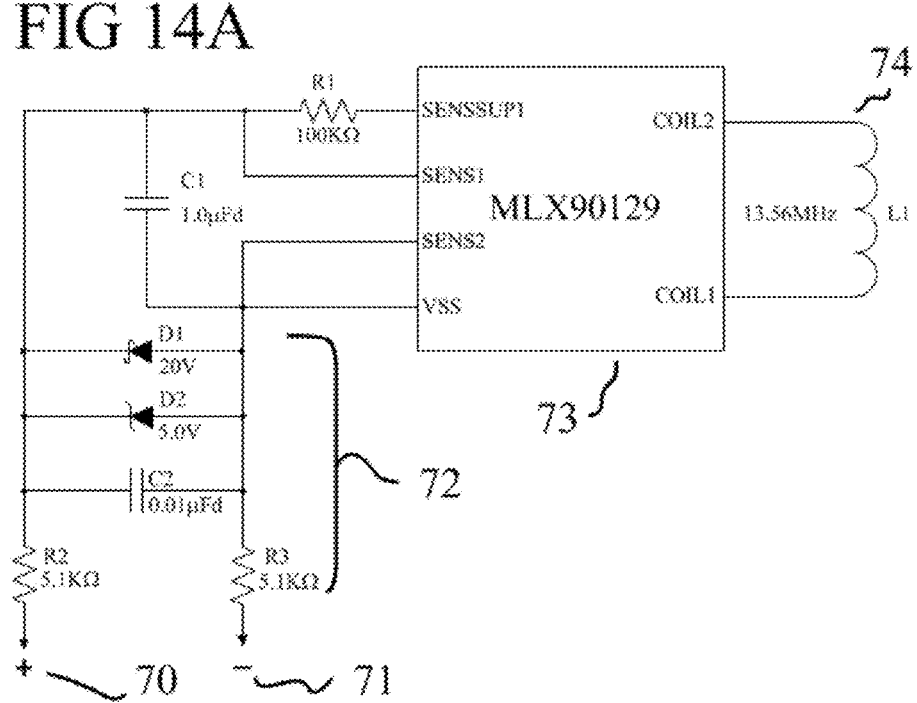
FIG. 14A shows a simplified electronic schematic of a proof-of-concept circuit using an existing RFID sensor chip.

FIG. 14A provides the schematic design for a prototype FIG. 13 device. A Melexis Semiconductor MLX90129 13.56 MHz RFID sensor tag integrated circuit 73 operating in passive RFID mode is used to realize the FIG. 13 functional elements 61, 66, 68 and 69, while the rest of the FIG. 13 functions are created using discrete passive electronic components. The device is connected to the waterproofing membrane 1 of FIG. 1B at the negative 71 and positive 70 connection points. The FIG. 13 protection circuit 62 is realized by FIG. 14A item 72, where Transient Voltage Suppression (TVS) diode D2 provides positive voltage protection by clamping the voltage across the positive 70 and negative 71 connection points at approximately +5 VDC, and the Schottky barrier diode D1 provides reverse polarity voltage protection for positive voltage appearing at the negative 71 connection point by clamping voltage at approximately +0.2V. Resistors R2 and R3 provide current limiting protection when either D1 or D2 are conducting current when suppressing voltage transients. Together, R2, R3, D1 and D2 will protect the MLX90129 RFID chip 73 against an 1000V surge appearing at either the positive 70 and negative 71 connection points and will offer protection up to 10 KV for very short durations (<100 μsec). Capacitors C1 and C2 with resistors R2 and R3 provide a modest level of higher frequency noise voltage suppression. When self-powered through the L1 antenna coil 74 by an external RFID reader device, the MLX90129 RFID chip 73 provides a regulated voltage from its SENSSUP1 pin of 3.0±0.1 VDC, which appears at the positive 70 connection point when no current is flowing through resistor R1. The MLX90129 RFID chip 73 VSS pin is referenced to the negative 71 connection point. Resistor R1 and the $R_M$ resistance of the rubberized asphalt waterproofing membrane 4 in FIG. 12 form a voltage divider, which converts the leakage current through the rubberized asphalt waterproofing membrane 4 to a voltage between differential input pins SENS1 and SENS2 of the MLX90129 RFID chip 73, where an internal signal conditioning circuit provides the voltage to the processing unit of the MLX90129 RFID chip 73.

Figure 14B:
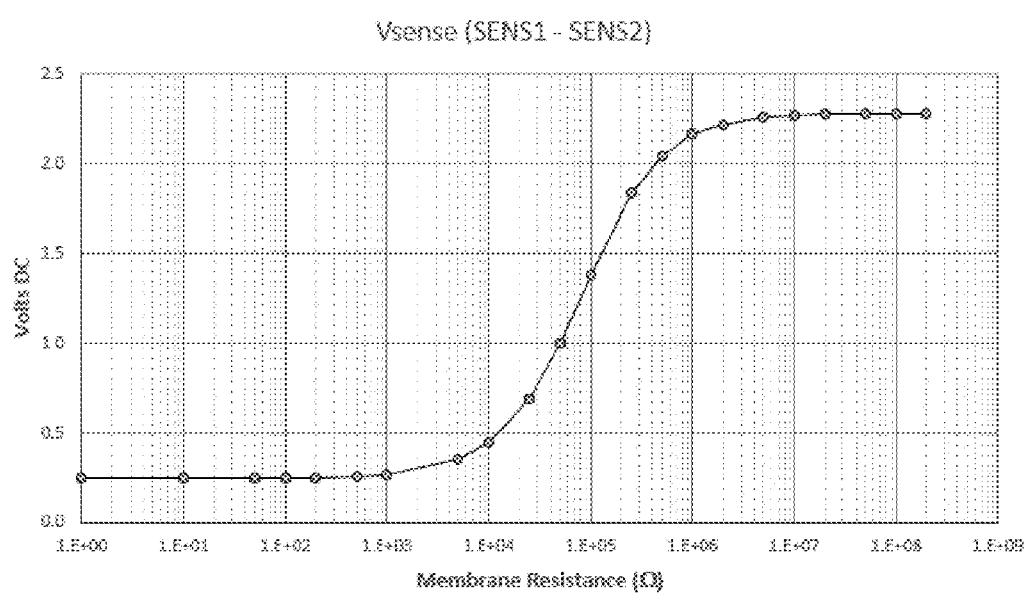
FIG. 14B shows the output response for the proof-of-concept circuit shown in FIG. 14A.

FIG. 14B shows the voltage relationship between rubberized asphalt waterproofing membrane 4 resistance and the Vsense (SENS1–SENSE2) DC voltage. Notice that at 200 Mohms (2.E+08 ohms) the Vsense voltage is approximately 2.28 VDC, and then drops rapidly when the rubberized asphalt waterproofing membrane 4 resistance changes between 1 Mohm (1.E+06 ohms) and 1 Kohms (1.E+03 ohms) leveling off at approximately 0.25 VDC. Because this device is intended to detect a leakage of water through the rubberized asphalt waterproofing membrane, this response characteristic provides a satisfactory leak-detection output. The circuit configuration shown in FIG. 14A could be modified to provide more instrumentation-like ohmmeter capability, but at the expense of greater power draw from the L1 antenna coil 74, which would act to reduce the range from which the reader could obtain information. Using back scattering, the voltage value measured by the MLX90129 RFID chip 73 between its SENS1 and SENS2 pins, is clocked back to the external RFID reader device through the RF link as an encoded serial digital signal.

The MLX90129 RFID chip 73 will respond to commands transmitted by the external RFID reader device and will transmit its unique ID, the voltage across SENSE1 and SENSE2, or the reading from an internal temperature sensor embedded within the chip. Because the MLX90129 uses anti-collision technology, multiple MLX90129 devices can be simultaneously interrogated by a single external RFID reader device. When assigned to a waterproofing panel, the MLX90129 device associated with that particular panel will be identified by the unique ID code stored in the MLX90129 RFID chip 73 that provides a specific address for each panel in a waterproofing installation, from which data can be acquired and recorded for future reference. In a final product configuration, the RFID sensor tag represented in FIG. 14A will be approximately the size and shape of a credit card, with the antenna 74 taking up most of the area.

The MLX90129 RFID chip 73 operates in the 13.56 MHz Industrial Scientific and Medical (ISM) worldwide band and allows a remote reader to obtain data from a distance between 1 and 3 meters; with the configuration shown in FIG. 14A, with the MLX90129 RFID chip 73 external memory and other non-essential devices either not installed or disabled, the range is closer to 3 meters with the proper antenna orientation. This will enable an operator with a hand-held reader with data storage capability to walk beside the building foundation and gather waterproofing system verification data keyed by the RFID address which will be tied to waterproofing panel location. If a RFID leak sensor tag is used that operates in the ISM 902-928 MHz frequency range, the range would be extended up to 12 meters, which would enable either a remotely located or several remotely located fixed position readers to be used for continuously gathering verification data from the waterproofing system.

It should be recognized that those skilled in the art of electronic design will be able to create many different leakage detection circuit sensor configurations with a variety of remote readers that will provide the functionality of the device shown in FIG. 13; furthermore, it would also be possible to combine the functions of the frequency optimized LCR device described in FIG. 11A with the leak detection device of FIG. 13.

In summary, the invention is directed to a waterproofing panel assembly. The waterproofing assembly comprises a composite waterproofing membrane, a drain board core, a filter fabric over the drain board. The composite waterproofing membrane has (a) a rubberized asphalt layer, the rubberized asphalt layer has a proximal surface side and a distal surface side, wherein the proximal side surface is positioned, relative to the distal surface side, closest to a building's surface, (b) a pressure sensitive rubberized asphalt adhesive coating under, relative to the proximal surface side being designated the composite waterproofing membrane's base, the proximal surface side, (c) a film backing positioned over the distal surface side, and (d) an electrically-conductive membrane layer with metal strips is between the rubberized asphalt layer and the film backing. The drain board core is over the film backing. There can also be (e) an electrical conduit that couples the electrically-conductive membrane layer or metal strips to an electrical condition measurement device. The electrical condition measurement device measures an external resistance to provide (a) intrinsic leak detection capability, (b) monitoring a functional topography of the composite waterproofing membrane, (c) an inference to confirm whether the composite waterproofing membrane contacts the building's surface, and (d) combinations thereof. In addition, the waterproofing panel assembly can further comprise a conductive primer positioned between the proximal surface side and the building's surface, and an electrical conduit that couples the conductive primer to an electrical condition measurement device, the electrical condition measurement device measures an external resistance to provide (a) intrinsic leak detection capability, (b) monitoring a functional topography of the composite waterproofing membrane, (c) an inference to confirm whether the composite waterproofing membrane contacts the building's surface, and (d) combinations thereof.

The electrical condition measurement device is selected from the group consisting of a hand-held ohmmeter, a capacitance measurement using an LCR meter, and a permanently wired voltage and leakage current device.

The waterproofing panel assembly appends, attaches, adheres, secures or connects to the building's surface without penetrating the composite waterproofing membrane. The waterproofing panel assembly contacts soil, sand, rocks, gravel, clay, water or combinations thereof, and wherein the building's surface is selected from the group consisting of a basement floor, a slab, a subterranean basement vertical wall, a partially subterranean basement vertical wall, a basement vertical wall, a slab's side surface.

The waterproofing panel assembly can also comprise an anti-abrasion layer over the filter fabric.

The method of installing the waterproofing panel assembly comprises appending, attaching, adhering, securing or connecting a waterproofing panel assembly to a building's surface without penetrating the composite waterproofing membrane and applying pressure to the waterproofing panel assembly. The method also entails connecting the electrical conduit that couples the electrically-conductive membrane layer or metal strips to the electrical condition measurement device or applying the conductive primer positioned under the interior surface side, and connecting the electrical conduit that couples the electrically-conductive membrane layer or metal strips to the electrical condition measurement device or connecting the second electrical conduit to the electrically-conductive membrane layer or metal strips to the electrical condition measurement device.

While this invention has been described in conjunction with preferred embodiments thereof, it is evident that many alternatives, modifications, and variations will be apparent to those skilled in the art. Accordingly, the present invention is intended to embrace all such alternatives, modifications and variations that fall within the broad scope of the appended claims.

We claim:

1. A waterproofing panel assembly comprising:
    a composite waterproofing membrane, the composite waterproofing membrane having:
    a rubberized asphalt layer, the rubberized asphalt layer has a proximal surface side and a distal surface side, wherein the proximal side surface is positioned, relative to the distal surface side, closest to a building's surface,
    a pressure sensitive rubberized asphalt adhesive coating under, relative to the proximal surface side being designated the composite waterproofing membrane's base, the proximal surface side,
    a film backing positioned over the distal surface side, and
    an electrically-conductive membrane layer with metal strips is between the rubberized asphalt layer and the film backing;
    a drain board core over the film backing;
    a filter fabric over the drain board; and
    an anti-abrasion layer over the filter fabric;
    wherein said anti-abrasion layer includes a bend-relief feature in the form of a plurality of traverse creases that provide said waterproofing panel with longitudinal flexibility to facilitate storage and shipment in rolls.

2. The waterproofing panel assembly of claim 1, further comprising:
    an electrical conduit that couples the electrically-conductive membrane layer or metal strips to an electrical condition measurement device, the electrical condition measurement device capable of measuring the capacitance between said electrically-conductive membrane and a substrate configuration to provide:
    (a) intrinsic leak-detection capability by measuring dielectric permittivity of the layers of said waterproofing panel assembly,
    (b) monitoring a functional topography of the composite waterproofing membrane,
    (c) an inference to confirm whether the composite waterproofing membrane contacts the building's surface, and
    (d) combinations thereof.

3. The waterproofing panel assembly of claim 1, further comprising:
    a conductive primer positioned between the proximal surface side and the building's surface; and
    an electrical conduit that couples the conductive primer to an electrical condition measurement device, the electrical condition measurement device capable of measuring the capacitance between said electrically-conductive membrane and an electrically primed substrate to provide:
    (a) intrinsic leak-detection capability by measuring dielectric permittivity of the layers of said waterproofing panel assembly,
    (b) monitoring a functional topography of the composite waterproofing membrane,
    (c) an inference to confirm whether the composite waterproofing membrane contacts the building's surface, and
    (d) combinations thereof.

4. The waterproofing panel assembly of claim 2, wherein the electrical condition measurement device is an LCR meter.

5. The waterproofing panel assembly of claim 3, wherein the electrical condition measurement device is an LCR meter.

6. The waterproofing panel assembly of claim 1, wherein the waterproofing panel assembly appends to the building's surface without penetrating the composite waterproofing membrane.

7. The waterproofing panel assembly of claim 6, wherein:
    the waterproofing panel assembly contacts soil, sand, rocks, gravel, clay, water, or combinations thereof; and
    the building's surface is selected from the group consisting of a basement floor, a slab, a subterranean basement vertical wall, a partially subterranean basement vertical wall, a basement vertical wall, and a slab's side surface.

8. The waterproofing panel assembly of claim 1, wherein said anti-abrasion layer is perforated and made from a material selected from the group comprising high-impact polystyrene and any functionally equivalent fungus-resistant and rot-resistant material.

9. A method of installing a waterproofing panel assembly comprising the steps of: appending a waterproofing panel assembly to a building's surface without penetrating a composite waterproofing membrane, the waterproofing panel assembly having;
    a composite waterproofing membrane, the composite waterproofing membrane having;
    a rubberized asphalt layer, the rubberized asphalt layer has a proximal surface side and a distal surface side, wherein the proximal side surface is positioned, relative to the distal surface side, closest to a building's surface,
    a pressure sensitive rubberized asphalt adhesive coating under, relative to the proximal surface side being designated the composite waterproofing membrane's base, the proximal surface side,
    a film backing positioned over the distal surface side, and an electrically-conductive membrane layer with metal strips is between the rubberized asphalt layer and the film backing, a drain board core over the film backing;

a filter fabric over the drain board; and an anti-abrasion layer over the filter fabric;

wherein said anti-abrasion layer includes a bend-relief feature in the form of a plurality of traverse creases that provide said waterproofing panel with longitudinal flexibility to facilitate storage and shipment in rolls; and applying pressure to the waterproofing panel assembly.

10. The method of claim 9, further comprising the steps of:

connecting an electrical conduit that couples the electrically-conductive membrane layer or metal strips to an electrical condition measurement device, the electrical condition measurement device capable of measuring the capacitance between said electrically-conductive membrane and a substrate configuration to provide:
  (a) intrinsic leak-detection capability by measuring dielectric permittivity of the layers of said waterproofing panel assembly,
  (b) monitoring a functional topography of the composite waterproofing membrane,
  (c) an inference to confirm whether the composite waterproofing membrane contacts the building's surface, and
  (d) combinations thereof.

11. The method of claim 9, further comprising the steps of:

applying a conductive primer positioned under the interior surface side; and connecting an electrical conduit that couples the conductive primer to an electrical condition measurement device, the electrical condition measurement device capable of measuring the capacitance between said electrically-conductive membrane and an electrically primed substrate to provide:
  (a) intrinsic leak-detection capability by measuring dielectric permittivity of the layers of said waterproofing panel assembly,
  (b) monitoring a functional topography of the composite waterproofing membrane,
  (c) an inference to confirm whether the composite waterproofing membrane contacts the building's surface, and
  (d) combinations thereof.

12. The method of claim 11, further comprising the step of connecting a second electrical conduit to the electrically-conductive membrane layer or metal strips to the electrical condition measurement device.

13. The method of claim 10, wherein the electrical condition measurement device is an LCR meter.

14. The method of claim 11, wherein the electrical condition measurement device is an LCR meter.

15. The method of claim 9, wherein the waterproofing panel assembly appends to the building's surface without penetrating the composite waterproofing membrane.

16. The method of claim 9, wherein:

the waterproofing panel assembly contacts soil, sand, rocks, gravel, clay, water, or combinations thereof; and the building's surface is selected from the group consisting of a basement floor, a slab, a subterranean basement vertical wall, a partially subterranean basement vertical wall, a basement vertical wall, and a slab's side surface.

17. The method of claim 9, wherein said anti-abrasion layer is perforated and made from a material selected from the group comprising high-impact polystyrene and any functionally equivalent fungus-resistant and rot-resistant material.

18. The method of claim 9, wherein the waterproofing assembly attaches through strings or tie-wraps positioned in a scaffolding cross member's opening.

19. The waterproofing panel assembly of claim 1, wherein the waterproofing assembly attaches through strings or tie-wraps positioned in a scaffolding cross member's opening.

* * * * *